(12) United States Patent
Duan et al.

(10) Patent No.: US 8,075,694 B2
(45) Date of Patent: *Dec. 13, 2011

(54) ACID FUNGAL PROTEASE IN FERMENTATION OF INSOLUBLE STARCH SUBSTRATES

(75) Inventors: Gang Duan, Shanghai (CN); Nigel Dunn-Coleman, El Sauzal (ES); Oreste Lantero, Trimble, MO (US); Craig E. Pilgrim, Roscoe, IL (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 359 days.

This patent is subject to a terminal disclaimer.

(21) Appl. No.: 12/485,767

(22) Filed: Jun. 16, 2009

(65) Prior Publication Data

US 2009/0317872 A1 Dec. 24, 2009

Related U.S. Application Data

(62) Division of application No. 11/314,987, filed on Dec. 21, 2005, now Pat. No. 7,563,607.

(60) Provisional application No. 60/640,399, filed on Dec. 30, 2004, provisional application No. 60/648,233, filed on Jan. 27, 2005.

(51) Int. Cl.
 C08B 37/00 (2006.01)
 C12C 1/00 (2006.01)
(52) U.S. Cl. .......................... 127/36; 435/93
(58) Field of Classification Search .............. 435/93; 127/36
 See application file for complete search history.

(56) References Cited

U.S. PATENT DOCUMENTS

| | | | |
|---|---|---|---|
| 4,092,434 A | 5/1978 | Yoshizumi et al. |
| 4,514,496 A | 4/1985 | Yoshizumi et al. |
| RE32,153 E | 5/1986 | Tamura et al. |
| 4,587,215 A | 5/1986 | Hirsh |
| 4,863,864 A | 9/1989 | Ashikari et al. |
| 5,093,257 A | 3/1992 | Gray |
| 5,231,017 A | 7/1993 | Lantero et al. |
| 5,278,059 A | 1/1994 | Sugimoto et al. |
| 5,545,587 A | 8/1996 | Sugimoto et al. |
| 5,736,499 A | 4/1998 | Mitchinson et al. |
| 5,874,276 A | 2/1999 | Fowler et al. |
| 5,958,739 A | 9/1999 | Mitchinson et al. |
| 6,022,725 A | 2/2000 | Fowler et al. |
| 6,093,562 A | 7/2000 | Bigard-Frantzen et al. |
| 6,254,914 B1 | 7/2001 | Singh et al. |
| 6,255,115 B1 | 7/2001 | Beijersbergen et al. |
| 6,268,328 B1 | 7/2001 | Mitchinson et al. |
| 6,352,851 B1 | 3/2002 | Nielsen et al. |
| 6,408,105 B1 | 6/2002 | Maruo |
| 6,436,888 B1 | 8/2002 | Svendsen et al. |
| 6,566,125 B2 | 5/2003 | Johnston et al. |
| 6,605,458 B1 | 8/2003 | Hansen et al. |
| 6,768,001 B2 | 7/2004 | Saloheimo et al. |
| 6,867,031 B2 | 3/2005 | Bigard-Frantzen et al. |
| 6,899,910 B2 | 5/2005 | Johnston et al. |
| 6,936,110 B2 | 8/2005 | Van Thorre |
| 6,936,294 B2 | 8/2005 | Matthews et al. |
| 2005/0266543 A1 | 12/2005 | Dunn-Coleman et al. |

FOREIGN PATENT DOCUMENTS

| | | |
|---|---|---|
| EP | 0 171 218 | 7/1985 |
| EP | 0 215 594 | 8/1986 |
| WO | WO 84/02921 | 8/1984 |
| WO | WO 92/00381 | 1/1992 |
| WO | WO 96/23874 | 8/1996 |
| WO | WO 96/39528 | 12/1996 |
| WO | WO 99/28488 | 6/1999 |
| WO | WO 99/34011 | 7/1999 |
| WO | WO 03/066826 | 8/2003 |
| WO | WO 03/068976 | 8/2003 |
| WO | WO 2004/080923 | 9/2004 |
| WO | WO 2004/081193 | 9/2004 |
| WO | WO 2004/106533 | 12/2004 |
| WO | WO 2004/111218 | 12/2004 |
| WO | WO 2004/113551 | 12/2004 |
| WO | WO 2005/001064 | 1/2005 |
| WO | WO 2005/003337 | 1/2005 |
| WO | WO 2005/052148 | 6/2005 |
| WO | WO 2005/087938 | 9/2005 |
| WO | WO 2006/073839 | 7/2006 |

OTHER PUBLICATIONS

Allison, Daniel S. et al., << Transformation of the thermophilic fungus Humicola grisea var. thermoidea and overproduction of Humicola glucoamylase, >> Current Genetics, vol. 21, pp. 225-229, 1992.

Altschul et al., "Basic Local Alignment Statistics, Methods in Enzymology", V. 266, pp. 460-480 (1993).

Ashikari, Toshihiko et al., << Rhizopus Raw-Starch-Degrading Glucoamylase : Its Cloning and Expression in Yeast, >> Agric. Biol. Chem., vol. 50, No. 4, pp. 957-964, 1986.

Bajar, Aslam, et al., "Identification of a fungal cutinase promoter that is inducible by a plant signal via a phosphorylated trans-acting factor," Proc. Natl. Acad. Sci. USA, vol. 88, pp. 8208-8212, Sep. 1991.

Boel, E. et al., << Glucoamylases G1 and G2 from Aspergillus niger are synthesized from two different but closely related mRNAs, >> The EMBO Journal, vol. 3, No. 5, pp. 1097-1102, 1984.

Boel, E. et al., << Two different types of intervening sequences in the glucoamylase gene from Aspergillus niger, >> The EMBO Journal, vol. 3, No. 7, pp. 1581-1585, 1984.

(Continued)

Primary Examiner — Jon P Weber
Assistant Examiner — Thane Underdahl

(57) ABSTRACT

The invention is directed to methods of producing ethanol and decreasing residual starch production in a no cook fermentation comprising contacting granular starch containing substrates with a granular starch hydrolyzing enzyme, a protease, and a fermenting microorganism under suitable fermentation conditions at a temperature below the starch gelatinization temperature of the starch substrate to produce ethanol, wherein the ethanol production is increased and the amount of residual starch is decreased compared to a substantially similar method conducted without the protease.

11 Claims, 9 Drawing Sheets

OTHER PUBLICATIONS

Brigidi, DeRossi, Bertarini, Riccardi and Matteuzzi, (1990), *FEMS Microbiol. Lett.* 67: 135-138.

Campos et al., "Purification and Characterization of a Glucoamylase from *Humicola grisea*," *Applied and Envir. Micro.*, Jun. 1995, p. 2436-2438.

Chen, Hsiu-mei et al., "Identification and elimination by site-directed mutagenesis of thermolabile aspartyl bonds in *Aspergillus awamori* glucoamylase," *Protein Engineering*, vol. 8, No. 6, pp. 575-582, 1995.

Chen, Hsiu-mei et al., << Effect of replacing helical glycine residues with alanines on reversible and irreversible stability and production of *Aspergillus awamori* glucoamylase, *Protein Engineering*, vol. 9, No. 6, pp. 499-505, 1996.

Chen, Frank Y. et al., "Regulation of mammalian ribonucleotide reductase R1 mRNA stability is mediated by a ribonucleotide reductase R1 mRNA 3'-untranslated region cis-trans interaction through a protein kinase C-controlled pathway, " *Biochem. J.*, vol. 302, pp. 125-132, 1994.

Database EMBL pp. 1-2, Mar. 1, 2001, Delgado-Jarana et al., "Putative aspartate protease", retrieved from EBI Datagase accession No. Q9HDT6.

Database EMBL pp. 1-2, Oct. 25, 2004 Viterbo et al., "Aspartyl protease" retrieved from EBI Database accession No. Q641D0.

Database EMBL pp. 1-3, Dec. 7, 2005, Mantyla, "*Hypocrea jecorina* proA gene for aspartic protease, exons 1-2, strain QM6a", retrieved from EBI Database accession No. AM168137.

Dayhoff et al., "A Model of Evolutionary Change in Proteins," *Atlas of Protein Sequence and Structure* 5:Suppl. 3 (National Biomedical Research Foundation, Washington, D.C. (1978).

Eneyskaya et al., "Acid protease from richoderma reesei : limited proteolysis of fungal carbohydrases," *Applied Microbiology and Biotechnology*, V. 52, 1999, pp. 226-231.

Fernandez-Abalos et al., "Posttranslational processing of the xylanase Xys1L from *Streptomyces halstedii* JM8 is carried out by secreted serine proteases," *Microbiology*, 2003, 149, 1623-1632.

Finkelstein, David B. et al., "Biotechnology of Filamentous Fungi," Technology and Products, Butterworth-Heinemann, David Finkelstein, ed., pp. 113-156, 1992.

Goldman, et al., "Transformation of *Trichoderma harzianum* by high-voltage electric pulse," *Current Genetics*, 17:169-174, 1990.

Han et al.m "Amylolysis of Raw Corn by *Aspergillus niger* for Simultaneous Ethaol Fermentation," *Biot. & Bioeng.*, V30, pp. 225-232 (1987).

Hata, Yoji et al., << The Glucoamylase cDNA from *Aspergillus oryzae* : Its Cloning, Nucleotide Sequence, and Expression in *Saccharomyces cerevisiae*, >> Agric. Biol. Chem., vol. 55, No. 4, pp. 941-949, 1991.

International Search Report for PCT/US2005/046474, filed Dec. 21, 2005.

Jensen, Bo et al., << Purification of extracellular amylotic enzymes from the thermophilic fungus *Thermomyces lanuginosus*, Can. J. Microbiol., vol. 34, pp. 218-223.

Ponnampalam et al., "Effect of Germ and Fiber Removal on Production of Ethanol from Corn," *Applied Biochem and Biotech.*, V. 113-116, 2004.

Singh et al., "An Enzymatic Process for Corn Wet Milling," *Advances in Food and Nutrition Res.*, V. 48, pp. 151-171, 2004.

Singh et al., "Recovery of Fiber in the Corn Dry-Grind Ethanol Process : A Feedstock for Valuable Coproducts," *Cereal Chemistry*, V. 76,N.6, 1999.

Smith, et al.,"Comparison of Biosequences," *Adv. Appl. Math.* 2:482-489, 1981.

Takahashi et al., "Different Behavior towards Raw Starch of Three Forms of Glucoamylase from a *Rhizopus* Sp.,"*J. Biochem.*, 663-671, (1985).

Taylor, Pamela M. et al., << Some Properties of a Glucoamylase Produced by the Thermophilic Fungus *Humicola lanuginosa*, >> Carbohydrate Research, vol. 61, pp. 301-308, 1978.

Tosi, Luis Ricardo Orsini et al., << Purification and characterization of an extracellular glycoamylase from the thermophilic fungus *Humicola grisea* var. *thermoidea*, >> Can J. Microbiol., vol. 39, pp. 846-855, 1993.

Ueda et al., "Production of Ethanol from Raw Cassava Starch by a Nonconventional Fermentation Method," *Biotechnology and Bioengineering*, Vol. XXIII, 291-299, (1981).

Wang et al., "Comparison of enzymatic (E-Mill) and conventional dry=grind corn processes using a granular starch hydrolyzing enzyme," *Cereal Chemistry*, V. 82, Nov. 2005.

Yelton, et al., "Transformation of *Aspergillus nidulans* by using a *trpC* plasmid," *Proc. Natl. Acad. Sci.*, vol. 81, pp. 1470-1474, Mar. 1984.

FIGURE 1A (A) nsp24 polynucleotide sequence (SEQ ID NO: 1)

```
ATGCAGACCTTTGGAGCTTTTCTCGTTTCCTTCCTCGCCGCCAGCGGCCTGGCCGCGGCCCTCCC
CACCGAGGGTCAGAAGACGGCTTCCGTCGAGGTCCAGTACAACAAGAACTACGTCCCCCACGGCC
CTACTGCTCTCTTCAAGGCCAAGAGAAAGTATGGCGCTCCCATCAGCGACAACCTGAAGTCTCTC
GTGGCTGCCAGGCAGGCCAAGCAGGCTCTCGCCAAGCGCCAGACCGGCTCGGCGCCCAACCACCC
CAGTGACAGCGCCGATTCGGAGTACATCACCTCCGTCTCCATCGGCACTCCGGCTCAGGTCCTCC
CCCTGGACTTTGACACCGGCTCCTCCGACCTGTGGGTCTTTAGCTCCGAGACGCCCAAGTCTTCG
GCCACCGGCCACGCCATCTACACGCCCTCCAAGTCGTCCACCTCCAAGAAGGTGTCTGGCGCCAG
CTGGTCCATCAGCTACGGCGACGGCAGCAGCTCCAGCGGCGATGTCTACACCGACAAGGTCACCA
TCGGAGGCTTCAGCGTCAACACCCAGGGCGTCGAGTCTGCCACCCGCGTGTCCACCGAGTTCGTC
CAGGACACGGTCATCTCTGGCCTCGTCGGCCTTGCCTTTGACAGCGGCAACCAGGTCAGGCCGCA
CCCGCAGAAGACGTGGTTCTCCAACGCCGCCAGCAGCCTGGCTGAGCCCCTTTTCACTGCCGACC
TGAGGCACGGACAGAGTAAGTAGACACTCACTGGAATTCGTTCCTTTCCCGATCATCATGAAAGC
AAGTAGACTGACTGAACCAAACAACTAGACGGCAGCTACAACTTTGGCTACATCGACACCAGCGT
CGCCAAGGGCCCCGTTGCCTACACCCCCGTTGACAACAGCCAGGGCTTCTGGGAGTTCACTGCCT
CGGGCTACTCTGTCGGCGGCGGCAAGCTCAACCGCAACTCCATCGACGGCATTGCCGACACCGGC
ACCACCCTGCTCCTCCTCGACGACAACGTCGTCGATGCCTACTACGCCAACGTCCAGTCGGCCCA
GTACGACAACCAGCAGGAGGGTGTCGTCTTCGACTGCGACGAGGACCTCCCTTCGTTCAGCTTCG
GTGTTGGAAGCTCCACCATCACCATCCCTGGCGATCTGCTGAACCTGACTCCCCTCGAGGAGGGC
AGCTCCACCTGCTTCGGTGGCCTCCAGAGCAGCTCCGGCATTGGCATCAACATCTTTGGTGACGT
TGCCCTCAAGGCTGCCCTGGTTGTCTTTGACCTCGGCAACGAGCGCCTGGGCTGGGCTCAGAAAT
AA
```

FIGURE 1B (B) NSP24 amino acid sequence – 407 amino acids (SEQ ID NO: 2):

MQTFGAFLVSFLAASGLAAALPTEGQKTASVEVQYNKNYVPHGPTALFKAKRKYGAPISDNLKSL
VAARQAKQALAKRQTGSAPNHPSDSADSEYITSVSIGTPAQVLPLDFDTGSSDLWVFSSETPKSS
ATGHAIYTPSKSSTSKKVSGASWSISYGDGSSSSGDVYTDKVTIGGFSVNTQGVESATRVSTEFV
QDTVISGLVGLAFDSGNQVRPHPQKTWFSNAASSLAEPLFTADLRHGQNGSYNFGYIDTSVAKGP
VAYTPVDNSQGFWEFTASGYSVGGGKLNRNSIDGIADTGTTLLLLDDNVVDAYYANVQSAQYDNQ
QEGVVFDCDEDLPSFSFGVGSSTITIPGDLLNLTPLEEGSSTCFGGLQSSSGIGINIFGDVALKA
ALVVFDLGNERLGWAQK

FIGURE 2A pTrex3g_NSP24 nucleic acid sequence (SEQ ID NO: 4):

CTGCAGCCACTTGCAGTCCCGTGGAATTCTCACGGTGAATGTAGGCCTTTTGTAGGGTAGGAATT
GTCACTCAAGCACCCCCAACCTCCATTACGCCTCCCCCATAGAGTTCCCAATCAGTGAGTCATGG
CACTGTTCTCAAATAGATTGGGGAGAAGTTGACTTCCGCCCAGAGCTGAAGGTCGCACAACCGCA
TGATATAGGGTCGGCAACGGCAAAAAAGCACGTGGCTCACCGAAAAGCAAGATGTTTGCGATCTA
ACATCCAGGAACCTGGATACATCCATCATCACGCACGACCACTTTGATCTGCTGGTAAACTCGTA
TTCGCCCTAAACCGAAGTGCGTGGTAAATCTACACGTGGGCCCCTTTCGGTATACTGCGTGTGTC
TTCTCTAGGTGCCATTCTTTTCCCTTCCTCTAGTGTTGAATTGTTTGTGTTGGAGTCCGAGCTGT
AACTACCTCTGAATCTCTGGAGAATGGTGGACTAACGACTACCGTGCACCTGCATCATGTATATA
ATAGTGATCCTGAGAAGGGGGGTTTGGAGCAATGTGGGACTTTGATGGTCATCAAACAAAGAACG
AAGACGCCTCTTTTGCAAAGTTTTGTTTCGGCTACGGTGAAGAACTGGATACTTGTTGTGTCTTC
TGTGTATTTTTGTGGCAACAAGAGGCCAGAGACAATCTATTCAAACACCAAGCTTGCTCTTTTGA
GCTACAAGAACCTGTGGGTATATATCTAGAGTTGTGAAGTCGGTAATCCCGCTGTATAGTAATA
CGAGTCGCATCTAAATACTCCGAAGCTGCTGCGAACCCGGAGAATCGAGATGTGCTGGAAAGCTT
CTAGCGAGCGGCTAAATTAGCATGAAAGGCTATGAGAAATTCTGGAGACGGCTTGTTGAATCATG
GCGTTCCATTCTTCGACAAGCAAAGCGTTCCGTCGCAGTAGCAGGCACTCATTCCCGAAAAAACT
CGGAGATTCCTAAGTAGCGATGGAACCGGAATAATATAATAGGCAATACATTGAGTTGCCTCGAC
GGTTGCAATGCAGGGGTACTGAGCTTGGACATAACTGTTCCGTACCCCACCTCTTCTCAACCTTT
GGCGTTTCCTGATTCAGCGTACCCGTACAAGTCGTAATCACTATTAACCCAGACTGACCGGACG
TGTTTTGCCCTTCATTTGGAGAAATAATGTCATTGCGATGTGTAATTTGCCTGCTTGACCGACTG
GGGCTGTTCGAAGCCCGAATGTAGGATTGTTATCCGAACTCTGCTCGTAGAGGCATGTTGTGAAT
CTGTGTCGGGCAGGACACGCCTCGAAGGTTCACGGCAAGGGAAACCACCGATAGCAGTGTCTAGT
AGCAACCTGTAAAGCCGCAATGCAGCATCACTGGAAAATACAAACCAATGGCTAAAAGTACATAA
GTTAATGCCTAAAGAAGTCATATACCAGCGGCTAATAATTGTACAATCAAGTGGCTAAACGTACC
GTAATTTGCCAACGGCTTGTGGGGTTGCAGAAGCAACGGCAAAGCCCCACTTCCCCACGTTTGTT
TCTTCACTCAGTCCAATCTCAGCTGGTGATCCCCCAATTGGGTCGCTTGTTTGTTCCGGTGAAGT
GAAAGAAGACAGAGGTAAGAATGTCTGACTCGGAGCGTTTTGCATACAACCAAGGGCAGTGATGG
AAGACAGTGAAATGTTGACATTCAAGGAGTATTTAGCCAGGGATGCTTGAGTGTATCGTGTAAGG
AGGTTTGTCTGCCGATACGACGAATACTGTATAGTCACTTCTGATGAAGTGGTCCATATTGAAAT
GTAAGTCGGCACTGAACAGGCAAAAGATTGAGTTGAAACTGCCTAAGATCTCGGGCCCTCGGGCC
TTCGGCCTTTGGGTGTACATGTTTGTGCTCCGGGCAAATGCAAAGTGTGGTAGGATCGAACACAC
TGCTGCCTTTACCAAGCAGCTGAGGGTATGTGATAGGCAAATGTTCAGGGGCCACTGCATGGTTT
CGAATAGAAAGAGAAGCTTAGCCAAGAACAATAGCCGATAAAGATAGCCTCATTAAACGGAATGA
GCTAGTAGGCAAAGTCAGCGAATGTGTATATATAAAGGTTCGAGGTCCGTGCCTCCCTCATGCTC
TCCCCATCTACTCATCAACTCAGATCCTCCAGGAGACTTGTACACCATCTTTTGAGGCACAGAAA
CCCAATAGTCAACCATCACAAGTTTGTACAAAAAAGCAGGCTCCGCGGCCGCCCCCTTCACCATG
CAGACCTTTGGAGCTTTTCTCGTTTCCTTCCTCGCCGCCAGCGGCCTGGCCGCGGCCCTCCCCAC
CGAGGGTCAGAAGACGGCTTCCGTCGAGGTCCAGTACAACAAGAACTACGTCCCCCACGGCCCTA
CTGCTCTCTTCAAGGCCAAGAGAAAGTATGGCGCTCCCATCAGCGACAACCTGAAGTCTCTCGTG
GCTGCCAGGCAGGCCAAGCAGGCTCTCGCCAAGCGCCAGACCGGCTCGGCGCCCAACCACCCCAG
TGACAGCGCCGATTCGGAGTACATCACCTCCGTCTCCATCGGCACTCCGGCTCAGGTCCTCCCCC
TGGACTTTGACACCGGCTCCTCCGACCTGTGGGTCTTTAGCTCCGAGACGCCCAAGTCTTCGGCC
ACCGGCCACGCCATCTACACGCCCTCCAAGTCGTCCACCTCCAAGAAGGTGTCTGGCGCCAGCTG

FIGURE 2B

```
GTCCATCAGCTACGGCGACGGCAGCAGCTCCAGCGGCGATGTCTACACCGACAAGGTCACCATCG
GAGGCTTCAGCGTCAACACCCAGGGCGTCGAGTCTGCCACCCGCGTGTCCACCGAGTTCGTCCAG
GACACGGTCATCTCTGGCCTCGTCGGCCTTGCCTTTGACAGCGGCAACCAGGTCAGGCCGCACCC
GCAGAAGACGTGGTTCTCCAACGCCGCCAGCAGCCTGGCTGAGCCCCTTTTCACTGCCGACCTGA
GGCACGGACAGAGTAAGTAGACACTCACTGGAATTCGTTCCTTTCCCGATCATCATGAAAGCAAG
TAGACTGACTGAACCAAACAACTAGACGGCAGCTACAACTTTGGCTACATCGACACCAGCGTCGC
CAAGGGCCCCGTTGCCTACACCCCGTTGACAACAGCCAGGGCTTCTGGGAGTTCACTGCCTCGG
GCTACTCTGTCGGCGGCGGCAAGCTCAACCGCAACTCCATCGACGGCATTGCCGACACCGGCACC
ACCCTGCTCCTCCTCGACGACAACGTCGTCGATGCCTACTACGCCAACGTCCAGTCGGCCCAGTA
CGACAACCAGCAGGAGGGTGTCGTCTTCGACTGCGACGAGGACCTCCCTTCGTTCAGCTTCGGTG
TTGGAAGCTCCACCATCACCATCCCTGGCGATCTGCTGAACCTGACTCCCCTCGAGGAGGGCAGC
TCCACCTGCTTCGGTGGCCTCCAGAGCAGCTCCGGCATTGGCATCAACATCTTTGGTGACGTTGC
CCTCAAGGCTGCCCTGGTTGTCTTTGACCTCGGCAACGAGCGCCTGGGCTGGGCTCAGAAATAAA
AGGGTGGGCGCGCCGACCCAGCTTTCTTGTACAAAGTGGTGATCGCGCCAGCTCCGTGCGAAAGC
CTGACGCACCGGTAGATTCTTGGTGAGCCCGTATCATGACGGCGGCGGGAGCTACATGGCCCCGG
GTGATTTATTTTTTTTGTATCTACTTCTGACCCTTTTCAAATATACGGTCAACTCATCTTTCACT
GGAGATGCGGCCTGCTTGGTATTGCGATGTTGTCAGCTTGGCAAATTGTGGCTTTCGAAAACACA
AAACGATTCCTTAGTAGCCATGCATTTTAAGATAACGGAATAGAAGAAAGAGGAAATTAAAAAAA
AAAAAAAAACAAACATCCCGTTCATAACCCGTAGAATCGCCGCTCTTCGTGTATCCCAGTACCAG
TTTATTTTGAATAGCTCGCCCGCTGGAGAGCATCCTGAATGCAAGTAACAACCGTAGAGGCTGAC
ACGGCAGGTGTTGCTAGGGAGCGTCGTGTTCTACAAGGCCAGACGTCTTCGCGGTTGATATATAT
GTATGTTTGACTGCAGGCTGCTCAGCGACGACAGTCAAGTTCGCCCTCGCTGCTTGTGCAATAAT
CGCAGTGGGGAAGCCACACCGTGACTCCCATCTTTCAGTAAAGCTCTGTTGGTGTTTATCAGCAA
TACACGTAATTTAAACTCGTTAGCATGGGCTGATAGCTTAATTACCGTTTACCAGTGCCATGGT
TCTGCAGCTTTCCTTGGCCCGTAAAATTCGGCGAAGCCAGCCAATCACCAGCTAGGCACCAGCTA
AACCCTATAATTAGTCTCTTATCAACACCATCCGCTCCCCGGGATCAATGAGGAGAATGAGGGG
GATGCGGGGCTAAAGAAGCCTACATAACCCTCATGCCAACTCCCAGTTTACACTCGTCGAGCCAA
CATCCTGACTATAAGCTAACACAGAATGCCTCAATCCTGGGAAGAACTGGCCGCTGATAAGCGCG
CCCGCCTCGCAAAAACCATCCCTGATGAATGGAAAGTCCAGACGCTGCCTGCGGAAGACAGCGTT
ATTGATTTCCCAAAGAAATCGGGGATCCTTTCAGAGGCCGAACTGAAGATCACAGAGGCCTCCGC
TGCAGATCTTGTGTCCAAGCTGGCGGCCGGAGAGTTGACCTCGGTGGAAGTTACGCTAGCATTCT
GTAAACGGGCAGCAATCGCCCAGCAGTTAGTAGGGTCCCCTCTACCTCTCAGGGAGATGTAACAA
CGCCACCTTATGGGACTATCAAGCTGACGCTGGCTTCTGTGCAGACAAACTGCGCCCACGAGTTC
TTCCCTGACGCCGCTCTCGCGCAGGCAAGGGAACTCGATGAATACTACGCAAAGCACAAGAGACC
CGTTGGTCCACTCCATGGCCTCCCCATCTCTCTCAAAGACCAGCTTCGAGTCAAGGTACACCGTT
GCCCCTAAGTCGTTAGATGTCCCTTTTTGTCAGCTAACATATGCCACCAGGGCTACGAAACATCA
ATGGGCTACATCTCATGGCTAAACAAGTACGACGAAGGGGACTCGGTTCTGACAACCATGCTCCG
CAAAGCCGGTGCCGTCTTCTACGTCAAGACCTCTGTCCCGCAGACCCTGATGGTCTGCGAGACAG
TCAACAACATCATCGGGCGCACCGTCAACCCACGCAACAAGAACTGGTCGTGCGGCGGCAGTTCT
GGTGGTGAGGGTGCGATCGTTGGGATTCGTGGTGGCGTCATCGGTGTAGGAACGGATATCGGTGG
CTCGATTCGAGTGCCGGCCGCGTTCAACTTCCTGTACGGTCTAAGGCCGAGTCATGGGCGGCTGC
CGTATGCAAAGATGGCGAACAGCATGGAGGGTCAGGAGACGGTGCACAGCGTTGTCGGGCCGATT
ACGCACTCTGTTGAGGGTGAGTCCTTCGCCTCTTCCTTCTTTTCCTGCTCTATACCAGGCCTCCA
CTGTCCTCCTTTCTTGCTTTTTATACTATATACGAGACCGGCAGTCACTGATGAAGTATGTTAGA
CCTCCGCCTCTTCACCAAATCCGTCCTCGGTCAGGAGCCATGGAAATACGACTCCAAGGTCATCC
CCATGCCCTGGCGCCAGTCCGAGTCGGACATTATTGCCTCCAAGATCAAGAACGGCGGGCTCAAT
ATCGGCTACTACAACTTCGACGGCAATGTCCTTCCACACCCTCCTATCCTGCGCGGCGTGGAAAC
CACCGTCGCCGCACTCGCCAAAGCCGGTCACACCGTGACCCCGTGGACGCCATACAAGCACGATT
TCGGCCACGATCTCATCTCCCATATCTACGCGGCTGACGGCAGCGCCGACGTAATGCGCGATATC
```

FIGURE 2C

```
AGTGCATCCGGCGAGCCGGCGATTCCAAATATCAAAGACCTACTGAACCCGAACATCAAAGCTGT
TAACATGAACGAGCTCTGGGACACGCATCTCCAGAAGTGGAATTACCAGATGGAGTACCTTGAGA
AATGGCGGGAGGCTGAAGAAAAGGCCGGGAAGGAACTGGACGCCATCATCGCGCCGATTACGCCT
ACCGCTGCGGTACGGCATGACCAGTTCCGGTACTATGGGTATGCCTCTGTGATCAACCTGCTGGA
TTTCACGAGCGTGGTTGTTCCGGTTACCTTTGCGGATAAGAACATCGATAAGAAGAATGAGAGTT
TCAAGGCGGTTAGTGAGCTTGATGCCCTCGTGCAGGAAGAGTATGATCCGGAGGCGTACCATGGG
GCACCGGTTGCAGTGCAGGTTATCGGACGGAGACTCAGTGAAGAGAGGACGTTGGCGATTGCAGA
GGAAGTGGGGAAGTTGCTGGGAAATGTGGTGACTCCATAGCTAATAAGTGTCAGATAGCAATTTG
CACAAGAAATCAATACCAGCAACTGTAAATAAGCGCTGAAGTGACCATGCCATGCTACGAAAGAG
CAGAAAAAAACCTGCCGTAGAACCGAAGAGATATGACACGCTTCCATCTCTCAAAGGAAGAATCC
CTTCAGGGTTGCGTTTCCAGTCTAGACACGTATAACGGCACAAGTGTCTCTCACCAAATGGGTTA
TATCTCAAATGTGATCTAAGGATGGAAAGCCCAGAATATCGATCGCGCGCAGATCCATATATAGG
GCCCGGGTTATAATTACCTCAGGTCGACGTCCCATGGCCATTCGAATTCGTAATCATGGTCATAG
CTGTTTCCTGTGTGAAATTGTTATCCGCTCACAATTCCACACAACATACGAGCCGGAAGCATAAA
GTGTAAAGCCTGGGGTGCCTAATGAGTGAGCTAACTCACATTAATTGCGTTGCGCTCACTGCCCG
CTTTCCAGTCGGGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGCT
GCGGCGAGCGGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTG
GCGTTTTTCCATAGGCTCCGCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACTAGAAGAACAGTATT
TGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTGTTTGCAAGCAGCAGATTACGCGCAGAAAAAAA
GGATCTCAAGAAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTAAATTAAAAAT
GAAGTTTTAAATCAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGAGACC
CACGCTCACCGGCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTAGAGTAAGTAG
TTCGCCAGTTAATAGTTTGCGCAACGTTGTTGCCATTGCTACAGGCATCGTGGTGTCACGCTCGT
CGTTTGGTATGGCTTCATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAAGTAAGTTGGCCGCAGT
GTTATCACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGCA
AAAACAGGAAGGCAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATAT
TTGAATGTATTTAGAAAAATAAACAAATAGGGGTTCCGCGCACATTTCCCCGAAAAGTGCCACCT
GACGTCTAAGAAACCATTATTATCATGACATTAACCTATAAAAATAGGCGTATCACGAGGCCCTT
TCGTCTCGCGCGTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAGCGGGTGTTGGC
```

FIGURE 2D

```
GGGTGTCGGGGCTGGCTTAACTATGCGGCATCAGAGCAGATTGTACTGAGAGTGCACCATAAAAT
TGTAAACGTTAATATTTTGTTAAAATTCGCGTTAAATTTTTGTTAAATCAGCTCATTTTTTAACC
AATAGGCCGAAATCGGCAAAATCCCTTATAAATCAAAAGAATAGCCCGAGATAGGGTTGAGTGTT
GTTCCAGTTTGGAACAAGAGTCCACTATTAAAGAACGTGGACTCCAACGTCAAAGGGCGAAAAAC
CGTCTATCAGGGCGATGGCCCACTACGTGAACCATCACCCAAATCAAGTTTTTTGGGGTCGAGGT
GCCGTAAAGCACTAAATCGGAACCCTAAAGGGAGCCCCCGATTTAGAGCTTGACGGGGAAAGCCG
GCGAACGTGGCGAGAAAGGAAGGGAAGAAAGCGAAAGGAGCGGGCGCTAGGGCGCTGGCAAGTGT
AGCGGTCACGCTGCGCGTAACCACCACACCCGCCGCGCTTAATGCGCCGCTACAGGGCGCGTACT
ATGGTTGCTTTGACGTATGCGGTGTGAAATACCGCACAGATGCGTAAGGAGAAAATACCGCATCA
GGCGCCATTCGCCATTCAGGCTGCGCAACTGTTGGGAAGGGCGATCGGTGCGGGCCTCTTCGCTA
TTACGCCAGCTGGCGAAAGGGGATGTGCTGCAAGGCGATTAAGTTGGGTAACGCCAGGGTTTTC
CCAGTCACGACGTTGTAAAACGACGGCCAGTGCCCAAGCTTACTAGTACTTCTCGAGCTCTGTAC
ATGTCCGGTCGCGACGTACGCGTATCGATGGCGCCAGCTGCAGGCGGCCGC
```

US 8,075,694 B2

```
SEQUENCE LISTING

<160> NUMBER OF SEQ ID NOS: 6

<210> SEQ ID NO 1
<211> LENGTH: 1302
<212> TYPE: DNA
<213> ORGANISM: Trichoderma sp.

<400> SEQUENCE: 1
atgcagacct ttggagcttt tctcgtttcc ttcctcgccg ccagcggcct ggccgcggcc      60
ctccccaccg agggtcagaa gacggcttcc gtcgaggtcc agtacaacaa gaactacgtc     120
ccccacggcc ctactgctct cttcaaggcc aagagaaagt atggcgctcc catcagcgac     180
aacctgaagt ctctcgtggc tgccaggcag gccaagcagg ctctcgccaa gcgccagacc     240
ggctcggcgc ccaaccaccc cagtgacagc gccgattcgg agtacatcac ctccgtctcc     300
atcggcactc cggctcaggt cctcccctg  gactttgaca ccggctcctc cgacctgtgg     360
gtctttagct ccgagacgcc caagtcttcg gccaccggcc acgccatcta cacgccctcc     420
aagtcgtcca cctccaagaa ggtgtctggc gccagctggt ccatcagcta cggcgacggc     480
agcagctcca gcggcgatgt ctacaccgac aaggtcacca tcggaggctt cagcgtcaac     540 acccaggcg  tcgagtctgc cacccgcgtg tccaccgagt tcgtccagga cacggtcatc     600
tctggcctcg tcggccttgc ctttgacagc ggcaaccagg tcaggccgca cccgcagaag     660
acgtggttct ccaacgccgc cagcagcctg gtgagcccc  ttttcactgc cgacctgagg     720
cacggacaga gtaagtagac actcactgga attcgttcct ttcccgatca tcatgaaagc     780
aagtagactg actgaaccaa acaactagac ggcagctaca actttggcta catcgacacc     840
agcgtcgcca agggccccgt tgcctacacc cccgttgaca caagccaggg cttctgggag     900
```

-continued

```
ttcactgcct cgggctactc tgtcggcggc ggcaagctca accgcaactc catcgacggc    960
attgccgaca ccggcaccac cctgctcctc ctcgacgaca acgtcgtcga tgcctactac   1020
gccaacgtcc agtcggccca gtacgacaac cagcaggagg gtgtcgtctt cgactgcgac   1080
gaggacctcc cttcgttcag cttcggtgtt ggaagctcca ccatcaccat ccctggcgat   1140
ctgctgaacc tgactcccct cgaggagggc agctccacct gcttcggtgg cctccagagc   1200
agctccggca ttggcatcaa catctttggt gacgttgccc tcaaggctgc cctggttgtc   1260
tttgacctcg caacgagcg cctgggctgg gctcagaaat aa                       1302
```

<210> SEQ ID NO 2
<211> LENGTH: 407
<212> TYPE: PRT
<213> ORGANISM: Trichoderma sp.

<400> SEQUENCE: 2

```
Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
            20                  25                  30

Val Gln Tyr Asn Lys Asn Tyr Val Pro His Gly Pro Thr Ala Leu Phe
        35                  40                  45

Lys Ala Lys Arg Lys Tyr Gly Ala Pro Ile Ser Asp Asn Leu Lys Ser
    50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
                85                  90                  95

Thr Ser Val Ser Ile Gly Thr Pro Ala Gln Val Leu Pro Leu Asp Phe
            100                 105                 110

Asp Thr Gly Ser Ser Asp Leu Trp Val Phe Ser Ser Glu Thr Pro Lys
        115                 120                 125

Ser Ser Ala Thr Gly His Ala Ile Tyr Thr Pro Ser Lys Ser Ser Thr
    130                 135                 140

Ser Lys Lys Val Ser Gly Ala Ser Trp Ser Ile Ser Tyr Gly Asp Gly
145                 150                 155                 160

Ser Ser Ser Ser Gly Asp Val Tyr Thr Asp Lys Val Thr Ile Gly Gly
                165                 170                 175

Phe Ser Val Asn Thr Gln Gly Val Glu Ser Ala Thr Arg Val Ser Thr
            180                 185                 190

Glu Phe Val Gln Asp Thr Val Ile Ser Gly Leu Val Gly Leu Ala Phe
        195                 200                 205

Asp Ser Gly Asn Gln Val Arg Pro His Pro Gln Lys Thr Trp Phe Ser
    210                 215                 220

Asn Ala Ala Ser Ser Leu Ala Glu Pro Leu Phe Thr Ala Asp Leu Arg
225                 230                 235                 240

His Gly Gln Asn Gly Ser Tyr Asn Phe Gly Tyr Ile Asp Thr Ser Val
                245                 250                 255

Ala Lys Gly Pro Val Ala Tyr Thr Pro Val Asp Asn Ser Gln Gly Phe
            260                 265                 270

Trp Glu Phe Thr Ala Ser Gly Tyr Ser Val Gly Gly Lys Leu Asn
        275                 280                 285

Arg Asn Ser Ile Asp Gly Ile Ala Asp Thr Gly Thr Thr Leu Leu Leu
    290                 295                 300
```

```
Leu Asp Asp Asn Val Val Asp Ala Tyr Tyr Ala Asn Val Gln Ser Ala
305                 310                 315                 320

Gln Tyr Asp Asn Gln Gln Glu Gly Val Val Phe Asp Cys Asp Glu Asp
            325                 330                 335

Leu Pro Ser Phe Ser Phe Gly Val Gly Ser Ser Thr Ile Thr Ile Pro
            340                 345                 350

Gly Asp Leu Leu Asn Leu Thr Pro Leu Glu Glu Gly Ser Ser Thr Cys
            355                 360                 365

Phe Gly Gly Leu Gln Ser Ser Ser Gly Ile Gly Ile Asn Ile Phe Gly
370                 375                 380

Asp Val Ala Leu Lys Ala Ala Leu Val Val Phe Asp Leu Gly Asn Glu
385                 390                 395                 400

Arg Leu Gly Trp Ala Gln Lys
            405
```

<210> SEQ ID NO 3
<211> LENGTH: 355
<212> TYPE: PRT
<213> ORGANISM: Trichoderma sp.

<400> SEQUENCE: 3

```
Lys Tyr Gly Ala Pro Ile Ser Asp Asn Leu Lys Ser Leu Val Ala Ala
1               5                   10                  15

Arg Gln Ala Lys Gln Ala Leu Ala Lys Arg Gln Thr Gly Ser Ala Pro
            20                  25                  30

Asn His Pro Ser Asp Ser Ala Asp Ser Glu Tyr Ile Thr Ser Val Ser
            35                  40                  45

Ile Gly Thr Pro Ala Gln Val Leu Pro Leu Asp Phe Asp Thr Gly Ser
    50                  55                  60

Ser Asp Leu Trp Val Phe Ser Ser Glu Thr Pro Lys Ser Ser Ala Thr
65                  70                  75                  80

Gly His Ala Ile Tyr Thr Pro Ser Lys Ser Thr Ser Lys Lys Val
            85                  90                  95

Ser Gly Ala Ser Trp Ser Ile Ser Tyr Gly Asp Gly Ser Ser Ser Ser
            100                 105                 110

Gly Asp Val Tyr Thr Asp Lys Val Thr Ile Gly Gly Phe Ser Val Asn
            115                 120                 125

Thr Gln Gly Val Glu Ser Ala Thr Arg Val Ser Thr Glu Phe Val Gln
130                 135                 140

Asp Thr Val Ile Ser Gly Leu Val Gly Leu Ala Phe Asp Ser Gly Asn
145                 150                 155                 160

Gln Val Arg Pro His Pro Gln Lys Thr Trp Phe Ser Asn Ala Ala Ser
            165                 170                 175

Ser Leu Ala Glu Pro Leu Phe Thr Ala Asp Leu Arg His Gly Gln Asn
            180                 185                 190

Gly Ser Tyr Asn Phe Gly Tyr Ile Asp Thr Ser Val Ala Lys Gly Pro
            195                 200                 205

Val Ala Tyr Thr Pro Val Asp Asn Ser Gln Gly Phe Trp Glu Phe Thr
210                 215                 220

Ala Ser Gly Tyr Ser Val Gly Gly Lys Leu Asn Arg Asn Ser Ile
225                 230                 235                 240

Asp Gly Ile Ala Asp Thr Gly Thr Thr Leu Leu Leu Asp Asp Asn
            245                 250                 255

Val Val Asp Ala Tyr Tyr Ala Asn Val Gln Ser Ala Gln Tyr Asp Asn
            260                 265                 270
```

-continued

```
Gln Gln Glu Gly Val Val Phe Asp Cys Asp Glu Asp Leu Pro Ser Phe
        275                 280                 285
Ser Phe Gly Val Gly Ser Ser Thr Ile Thr Ile Pro Gly Asp Leu Leu
    290                 295                 300
Asn Leu Thr Pro Leu Glu Glu Gly Ser Ser Thr Cys Phe Gly Gly Leu
305                 310                 315                 320
Gln Ser Ser Ser Gly Ile Gly Ile Asn Ile Phe Gly Asp Val Ala Leu
                325                 330                 335
Lys Ala Ala Leu Val Val Phe Asp Leu Gly Asn Glu Arg Leu Gly Trp
            340                 345                 350
Ala Gln Lys
        355

<210> SEQ ID NO 4
<211> LENGTH: 9931
<212> TYPE: DNA
<213> ORGANISM: Artificial Sequence
<220> FEATURE:
<223> OTHER INFORMATION: pTrex3g_NSP24 plasmid

<400> SEQUENCE: 4
ctgcagccac ttgcagtccc gtggaattct cacggtgaat gtaggccttt tgtagggtag      60
gaattgtcac tcaagcaccc ccaacctcca ttacgcctcc cccatagagt tcccaatcag     120
tgagtcatgg cactgttctc aaatagattg gggagaagtt gacttccgcc cagagctgaa     180
ggtcgcacaa ccgcatgata tagggtcggc aacggcaaaa aagcacgtgg ctcaccgaaa     240
agcaagatgt ttgcgatcta acatccagga acctggatac atccatcatc acgcacgacc     300
actttgatct gctggtaaac tcgtattcgc cctaaaccga agtgcgtggt aaatctacac     360
gtgggcccct ttcggtatac tgcgtgtgtc ttctctaggt gccattcttt tccttcctc     420
tagtgttgaa ttgtttgtgt tggagtccga gctgtaacta cctctgaatc tctggagaat     480
ggtggactaa cgactaccgt gcacctgcat catgtatata atagtgatcc tgagaagggg     540
ggtttggagc aatgtgggac tttgatggtc atcaaacaaa gaacgaagac gcctcttttg     600
caaagttttg tttcggctac ggtgaagaac tggatacttg ttgtgtcttc tgtgtatttt     660
tgtggcaaca agaggccaga gacaatctat tcaaacacca agcttgctct tttgagctac     720
aagaacctgt ggggtatata tctagagttg tgaagtcggt aatcccgctg tatagtaata     780
cgagtcgcat ctaaatactc cgaagctgct gcgaacccgg agaatcgaga tgtgctggaa     840
agcttctagc gagcggctaa attagcatga aaggctatga gaaattctgg gacggcttg     900
ttgaatcatg gcgttccatt cttcgacaag caaagcgttc cgtcgcagta gcaggcactc     960
attcccgaaa aaactcggag attcctaagt agcgatggaa ccggaataat ataataggca    1020
atacattgag ttgcctcgac ggttgcaatg caggggtact gagcttggac ataactgttc    1080
cgtaccccac ctcttctcaa cctttggcgt ttccctgatt cagcgtaccc gtacaagtcg    1140
taatcactat taacccagac tgaccggacg tgttttgccc ttcatttgga gaaataatgt    1200
cattgcgatg tgtaatttgc ctgcttgacc gactggggct gttcgaagcc cgaatgtagg    1260
attgttatcc gaactctgct cgtagaggca tgttgtgaat ctgtgtcggg caggacacgc    1320
ctcgaaggtt cacggcaagg gaaaccaccg atagcagtgt ctagtagcaa cctgtaaagc    1380
cgcaatgcag catcactgga aaatacaaac caatggctaa aagtacataa gttaatgcct    1440
aaagaagtca taccagcg gctaataatt gtacaatcaa gtggctaaac gtaccgtaat    1500
ttgccaacgg cttgtggggt tgcagaagca acggcaaagc cccacttccc cacgtttgtt    1560
```

-continued

```
tcttcactca gtccaatctc agctggtgat cccccaattg ggtcgcttgt tgttccggt      1620 gaagtgaaag aagacagagg taagaatgtc tgactcggag cgttttgcat acaaccaagg    1680
gcagtgatgg aagacagtga atgttgaca ttcaaggagt atttagccag ggatgcttga     1740
gtgtatcgtg taaggaggtt tgtctgccga tacgacgaat actgtatagt cacttctgat   1800
gaagtggtcc atattgaaat gtaagtcggc actgaacagg caaaagattg agttgaaact   1860
gcctaagatc tcgggccctc gggccttcgg ccttgggtg tacatgtttg tgctccgggc    1920
aaatgcaaag tgtggtagga tcgaacacac tgctgccttt accaagcagc tgagggtatg   1980
tgataggcaa atgttcaggg gccactgcat ggtttcgaat agaaagagaa gcttagccaa   2040
gaacaatagc cgataaagat agcctcatta acggaatga gctagtaggc aaagtcagcg     2100
aatgtgtata tataaaggtt cgaggtccgt gcctccctca tgctctcccc atctactcat   2160
caactcagat cctccaggag acttgtacac catcttttga ggcacagaaa cccaatagtc   2220
aaccatcaca gtttgtaca aaaaagcagg ctccgcggcc gccccttca ccatgcagac     2280 cttttggagct tttctcgttt ccttcctcgc cgccagcggc ctggccgcgg cctcccac    2340 cgagggtcag aagacggctt ccgtcgaggt ccagtacaac aagaactacg tcccccacgg   2400
ccctactgct ctcttcaagg ccaagagaaa gtatggcgct cccatcagcg acaacctgaa   2460
gtctctcgtg gctgccaggc aggccaagca ggctctcgcc aagcgccaga ccggctcggc   2520
gcccaaccac cccagtgaca gcgccgattc ggagtacatc acctccgtct ccatcggcac   2580
tccggctcag gtcctccccc tggactttga caccggctcc tccgacctgt gggtcttag    2640 ctccgagacg cccaagtctt cggccaccgg ccacgccatc tacacgccct ccaagtcgtc   2700
cacctccaag aaggtgtctg cgccagctg gtccatcagc tacggcgacg gcagcagctc   2760
cagcggcgat gtctacaccg acaaggtcac catcggaggc ttcagcgtca acacccaggg   2820
cgtcgagtct gccaccccgcg tgtccaccga gttcgtccag gacacggtca tctctggcct   2880
cgtcggcctt gccttgaca gcggcaacca ggtcaggccg caccccgcaga agacgtggtt   2940 ctccaacgcc gccagcagcc tggctgagcc ccttttcact gccgacctga ggcacggaca   3000
gagtaagtag acactcactg gaattcgttc cttccccgat catcatgaaa gcaagtagac   3060
tgactgaacc aaacaactag acggcagcta caactttggc tacatcgaca ccagcgtcgc   3120
caagggcccc gttgcctaca cccccgttga caacagccag ggcttctggg agttcactgc   3180
ctcgggctac tctgtcggcg gcggcaagct caaccgcaac tccatcgacg gcattgccga   3240
caccggcacc accctgctcc tcctcgacga caacgtcgtc gatgcctact acgccaacgt   3300
ccagtcggcc cagtacgaca accagcagga gggtgtcgtc ttcgactgcg acgaggacct   3360 ccccttcgttc agcttcggtg ttggaagctc caccatcacc atccctggcg atctgctgaa   3420
cctgactccc ctcgaggagg gcagctccac ctgcttcggt ggcctccaga gcagctccgg   3480
cattggcatc aacatctttg tgacgttgc cctcaaggct gccctggttg tctttgacct    3540
cggcaacgag cgcctgggct gggctcagaa ataaagggt gggcgcgccg acccagcttt   3600
cttgtacaaa gtggtgatcg cgccagctcc gtgcgaaagc ctgacgcacc ggtagattct   3660
tggtgagccc gtatcatgac ggcggcggga gctacatggc cccgggtgat ttattttttt   3720
tgtatctact tctgacccctt ttcaaatata cggtcaactc atctttcact ggagatgcgg  3780
cctgcttggt attgcgatgt tgtcagcttg gcaaattgtg gctttcgaaa acacaaaacg   3840
attccttagt agccatgcat tttaagataa cggaatagaa gaaagaggaa attaaaaaaa   3900 aaaaaaaac aaacatcccg ttcataaccc gtagaatcgc cgctcttcgt gtatcccagt     3960
```

```
accagtttat tttgaatagc tcgcccgctg gagagcatcc tgaatgcaag taacaaccgt   4020
agaggctgac acggcaggtg ttgctaggga gcgtcgtgtt ctacaaggcc agacgtcttc   4080
gcggttgata tatatgtatg tttgactgca ggctgctcag cgacgacagt caagttcgcc   4140
ctcgctgctt gtgcaataat cgcagtgggg aagccacacc gtgactccca tctttcagta   4200
aagctctgtt ggtgtttatc agcaatacac gtaatttaaa ctcgttagca tggggctgat   4260
agcttaatta ccgtttacca gtgccatggt tctgcagctt ccttggccc gtaaaattcg    4320 gcgaagccag ccaatcacca gctaggcacc agctaaaccc tataattagt ctcttatcaa   4380
caccatccgc tcccccggga tcaatgagga gaatgagggg gatgcgggc taagaagcc     4440 tacataaccc tcatgccaac tcccagttta cactcgtcga gccaacatcc tgactataag   4500
ctaacacaga atgcctcaat cctgggaaga actggccgct gataagcgcg cccgcctcgc   4560
aaaaaccatc cctgatgaat ggaaagtcca gacgctgcct gcggaagaca gcgttattga   4620
tttcccaaag aaatcgggga tcctttcaga ggccgaactg aagatcacag aggcctccgc   4680
tgcagatctt gtgtccaagc tggcggccgg agagttgacc tcggtggaag ttacgctagc   4740
attctgtaaa cgggcagcaa tcgcccagca gttagtaggg tccctctac ctctcaggga    4800 gatgtaacaa cgccaccta tgggactatc aagctgacgc tggcttctgt gcagacaaac    4860
tgcgcccacg agttcttccc tgacgccgct ctcgcgcagg caagggaact cgatgaatac   4920
tacgcaaagc acaagagacc cgttggtcca ctccatggcc tccccatctc tctcaaagac   4980
cagcttcgag tcaaggtaca ccgttgcccc taagtcgtta gatgtccctt tttgtcagct   5040
aacatatgcc accagggcta cgaaacatca atgggctaca tctcatggct aaacaagtac   5100
gacgaagggg actcggttct gacaaccatg ctccgcaaag ccggtgccgt cttctacgtc   5160
aagacctctg tcccgcagac cctgatggtc tgcgagacag tcaacaacat catcgggcgc   5220
accgtcaacc cacgcaacaa gaactggtcg tgccggcggca gttctggtgg tgagggtgcg   5280
atcgttggga ttcgtggtgg cgtcatcggt gtaggaacgg atatcggtgg ctcgattcga   5340
gtgccggccg cgttcaactt cctgtacggt ctaaggccga gtcatgggcg gctgccgtat   5400
gcaaagatgg cgaacagcat ggagggtcag agacgcggtgc acagcgttgt cgggccgatt   5460
acgcactctg ttgagggtga gtccttcgcc tcttccttct tttcctgctc tataccaggc   5520
ctccactgtc ctccttttctt gcttttttata ctatatacga gaccggcagt cactgatgaa   5580
gtatgttaga cctccgcctc ttcaccaaat ccgtcctcgg tcaggagcca tggaaatacg    5640
actccaaggt catccccatg ccctggcgcc agtccgagtc ggacattatt gcctccaaga   5700
tcaagaacgg cgggctcaat atcggctact acaacttcga cggcaatgtc cttccacacc   5760
ctcctatcct gcgcggcgtg gaaaccaccg tcgccgcact cgccaaagcc ggtcacaccg   5820
tgaccccgtg gacgccatac aagcacgatt tcggccacga tctcatctcc catatctacg   5880
cggctgacgg cagcgccgac gtaatgcgcg atatcagtgc atccggcgag ccggcgattc   5940
caaatatcaa agacctactg aacccgaaca tcaaagctgt taacatgaac gagctctggg   6000
acacgcatct ccagaagtgg aattaccaga tggagtacct tgagaaatgg cgggaggctg   6060
aagaaaaggc cgggaaggaa ctggacgcca tcatcgcgcc gattacgcct accgctgcgg   6120
tacggcatga ccagttccgg tactatgggt atgcctctgt gatcaacctg ctggatttca   6180
cgagcgtggt tgttccggtt acctttgcgg ataagaacat cgataagaag aatgagagtt   6240
tcaaggcggt tagtgagctt gatgcccctcg tgcaggaaga gtatgatccg gaggcgtacc   6300
atggggcacc ggttgcagtg caggttatcg gacggagact cagtgaagag aggacgttgg   6360
```

```
cgattgcaga ggaagtgggg aagttgctgg gaaatgtggt gactccatag ctaataagtg    6420
tcagatagca atttgcacaa gaaatcaata ccagcaactg taaataagcg ctgaagtgac    6480
catgccatgc tacgaaagag cagaaaaaaa cctgccgtag aaccgaagag atatgacacg    6540
cttccatctc tcaaaggaag aatcccttca gggttgcgtt tccagtctag acacgtataa    6600
cggcacaagt gtctctcacc aaatgggtta tatctcaaat gtgatctaag gatggaaagc    6660
ccagaatatc gatcgcgcgc agatccatat atagggcccg ggttataatt acctcaggtc    6720
gacgtcccat ggccattcga attcgtaatc atggtcatag ctgtttcctg tgtgaaattg    6780
ttatccgctc acaattccac acaacatacg agccggaagc ataaagtgta aagcctgggg    6840
tgcctaatga gtgagctaac tcacattaat tgcgttgcgc tcactgcccg ctttccagtc    6900
gggaaacctg tcgtgccagc tgcattaatg aatcggccaa cgcgcgggga gaggcggttt    6960
gcgtattggg cgctcttccg cttcctcgct cactgactcg ctgcgctcgg tcgttcggct    7020
gcggcgagcg gtatcagctc actcaaaggc ggtaatacgg ttatccacag aatcagggga    7080
taacgcagga agaacatgt gagcaaaagg ccagcaaaag gccaggaacc gtaaaaaggc    7140
cgcgttgctg gcgtttttcc ataggctccg cccccctgac gagcatcaca aaaatcgacg    7200
ctcaagtcag aggtggcgaa acccgacagg actataaaga taccaggcgt ttccccctgg    7260
aagctccctc gtgcgctctc ctgttccgac cctgccgctt accggatacc tgtccgcctt    7320
tctcccttcg ggaagcgtgg cgctttctca gctcacgc tgtaggtatc tcagttcggt    7380
gtaggtcgtt cgctccaagc tgggctgtgt gcacgaaccc cccgttcagc ccgaccgctg    7440
cgccttatcc ggtaactatc gtcttgagtc caacccggta agacacgact tatcgccact    7500
ggcagcagcc actggtaaca ggattagcag agcgaggtat gtaggcggtg ctacagagtt    7560
cttgaagtgg tggcctaact acggctacac tagaagaaca gtatttggta tctgcgctct    7620
gctgaagcca gttaccttcg gaaaaagagt tggtagctct tgatccggca aacaaaccac    7680
cgctggtagc ggtggttttt ttgtttgcaa gcagcagatt acgcgcagaa aaaaaggatc    7740
tcaagaagat cctttgatct tttctacggg gtctgacgct cagtggaacg aaaactcacg    7800
ttaagggatt ttggtcatga gattatcaaa aaggatcttc acctagatcc ttttaaatta    7860
aaaatgaagt tttaaatcaa tctaaagtat atatgagtaa acttggtctg acagttacca    7920
atgcttaatc agtgaggcac ctatctcagc gatctgtcta tttcgttcat ccatagttgc    7980
ctgactcccc gtcgtgtaga taactacgat acgggagggc ttaccatctg gccccagtgc    8040
tgcaatgata ccgcgagacc cacgctcacc ggctccagat ttatcagcaa taaaccagcc    8100
agccggaagg gccgagcgca gaagtggtcc tgcaacttta tccgcctcca tccagtctat    8160
taattgttgc cgggaagcta gagtaagtag ttcgccagtt aatagtttgc gcaacgttgt    8220
tgccattgct acaggcatcg tggtgtcacg ctcgtcgttt ggtatggctt cattcagctc    8280
cggttcccaa cgatcaaggc gagttacatg atcccccatg ttgtgcaaaa aagcggttag    8340
ctccttcggt cctccgatcg ttgtcagaag taagttggcc gcagtgttat cactcatggt    8400
tatggcagca ctgcataatt ctcttactgt catgccatcc gtaagatgct tttctgtgac    8460
tggtgagtac tcaaccaagt cattctgaga atagtgtatg cggcgaccga gttgctcttg    8520
cccggcgtca atacgggata ataccgcgcc acatagcaga actttaaaag tgctcatcat    8580
tggaaaacgt tcttcgggc gaaaactctc aaggatctta ccgctgttga tccagttc     8640 gatgtaaccc actcgtgcac ccaactgatc ttcagcatct tttactttca ccagcgtttc    8700
tgggtgagca aaaacaggaa ggcaaaatgc cgcaaaaaag ggaataaggg cgacacggaa    8760
```

```
atgttgaata ctcatactct tccttttca atattattga agcatttatc agggttattg    8820
tctcatgagc ggatacatat ttgaatgtat ttagaaaaat aaacaaatag gggttccgcg    8880
cacatttccc cgaaaagtgc cacctgacgt ctaagaaacc attattatca tgacattaac    8940
ctataaaaat aggcgtatca cgaggcccct tcgtctcgcg cgtttcggtg atgacggtga    9000
aaacctctga cacatgcagc tcccggagac ggtcacagct tgtctgtaag cggatgccgg    9060
gagcagacaa gcccgtcagg gcgcgtcagc gggtgttggc gggtgtcggg gctggcttaa    9120
ctatgcggca tcagagcaga ttgtactgag agtgcaccat aaaattgtaa acgttaatat    9180
tttgttaaaa ttcgcgttaa attttgtta aatcagctca ttttttaacc aataggccga    9240
aatcggcaaa atcccttata aatcaaaaga atagcccgag ataggggttga gtgttgttcc    9300 agtttggaac aagagtccac tattaaagaa cgtggactcc aacgtcaaag ggcgaaaaac    9360
cgtctatcag ggcgatggcc cactacgtga accatcaccc aaatcaagtt ttttggggtc    9420
gaggtgccgt aaagcactaa atcggaaccc taaagggagc ccccgattta gagcttgacg    9480
gggaaagccg gcgaacgtgg cgagaaagga agggaagaaa gcgaaaggag cgggcgctag    9540
ggcgctggca agtgtagcgg tcacgctgcg cgtaaccacc acaccgccg cgcttaatgc    9600 gccgctacag ggcgcgtact atggttgctt tgacgtatgc ggtgtgaaat accgcacaga    9660
tgcgtaagga gaaaataccg catcaggcgc cattcgccat tcaggctgcg caactgttgg    9720
gaagggcgat cggtgcgggc ctcttcgcta ttacgccagc tggcgaaagg gggatgtgct    9780
gcaaggcgat taagttgggt aacgccaggg ttttcccagt cacgacgttg taaaacgacg    9840
gccagtgccc aagcttacta gtacttctcg agctctgtac atgtccggtc gcgacgtacg    9900
cgtatcgatg gcgccagctg caggcggccg c                                  9931
```

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
caccatgcag acctttggag ct                                             22

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ttatttctga gcccagccca g                                              21

ACID FUNGAL PROTEASE IN FERMENTATION OF INSOLUBLE STARCH SUBSTRATES

RELATED APPLICATIONS

The present application is a divisional of U.S. patent application Ser. No. 11/314,987 filed Dec. 21, 2005, now issued U.S. Pat. No. 7,563,607 and claims priority to U.S. Provisional Patent Application No. 60/640,399, entitled Acid Fungal Proteases, filed Dec. 30, 2004 and U.S. Provisional Patent Application No. 60/648,233, entitled Acid Fungal Proteases, filed Jan. 27, 2005, the contents of which are fully incorporated herein by reference.

FIELD OF THE INVENTION

The present invention relates to methods for producing alcohol, such as ethanol during fermentation of granular starch containing substrates. The invention also relates to the inclusion of an acid fungal protease in the fermentation, which results in an increase in the production of ethanol and in a decrease in the amount of residual starch produced during the fermentation compared to fermentation without the protease.

BACKGROUND OF THE INVENTION

Industrial fermentation processes predominately use glucose as a feedstock for the production of numerous end products, such as proteins, enzymes, amino acids, organic acids, alcohols, biochemicals, pharmaceuticals and the like. In many of these applications glucose is produced from the enzymatic conversion of substrates, which contain starch. Starch accumulates as microscopic granules in plant material and the partial crystalline nature of these granules imparts insolubility in cold water. As a result, many methods have been described for solubilizing starch granules. In particular, many methods have been described for converting starch containing substrates to alcohols, such as ethanol. These methods include direct and indirect heating prior to fermentations (STARCH CHEMISTRY AND TECHNOLOGY, Eds. R. L. Whistler et al., $2^{nd}$ Ed., (1984) Academic Press Inc; STARCH CONVERSION TECHNOLOGY Eds., G. M. A. Van Beynum et al., Food Science and Technology Series, Marcel Dekker Inc, NY; and THE ALCOHOL TEXTBOOK 3rd Ed., Eds. K. Jacques et al., (1999), Nottingham University Press). Due to temperature requirements direct and indirect heating methods are energy demanding. Therefore, more recent attention in the industrial fermentation arts and especially in alcohol fermentation has been directed to low energy processes for hydrolyzing granular starch. Low energy processes reduce the need for energy intensive liquefaction cooking steps (U.S. Pat. No. 4,514,496; Ueda et al., (1980) *J. Ferment. Tech.*, 58:237-242; Han et al., (1987) *Biotechnol. and Bioeng.*, 30:225-232; WO 03/066826; WO 03/068976; WO 04/106533; WO 04/081193; WO 05/052148; and US Patent Publication 2005/0266543). A number of novel enzyme compositions capable of hydrolyzing granular (uncooked) starch to produce fermentable glucose in alcohol fermentation processes have been introduced into the market place in the last few years, for example STARGEN (Genencor International Inc.). However, there still remains a need for additional and more effective starch conversion methods, which yield alcohols and high quality fermentation byproducts such as distillers' feeds.

The use of proteases in yeast fermentations has been shown to increase the yield and rate of ethanol production from liquefied starch substrates (U.S. Pat. No. 5,231,017). The NSP24 proteases of the present invention are not only novel proteases but also may be used to increase the ethanol production from insoluble starch substrates.

SUMMARY OF THE INVENTION

The present invention relates to NSP24 proteases having at least 85% sequence identity to SEQ ID NO: 2 and biologically active fragments thereof. In one embodiment, the invention pertains to an NSP24 protease having at least 98% sequence identity to SEQ ID NO: 2 and biologically active fragments thereof, such as SEQ ID NO: 3. In further embodiments, the invention relates to the use of NSP24 proteases in yeast fermentations to produce ethanol.

In one aspect, the invention relates to NSP24 protease compositions for use in hydrolysis of insoluble starch containing substrates, such as grains and/or fractionated components thereof.

In another aspect, the invention relates to NSP24 protease compositions for use in ethanol production from yeast fermentations.

In a further aspect, the invention relates to a method for producing ethanol comprising saccharifying a milled insoluble starch substrate with a granular starch hydrolyzing enzyme composition and an NSP24 protease at a temperature below the starch gelatinization temperature of the substrate and fermenting the saccharified starch substrate under suitable fermentation conditions to produce at least 8% v/v ethanol.

In another aspect, the invention relates to a method of increasing ethanol production in a no cook fermentation comprising contacting a milled insoluble starch substrate with a granular starch hydrolyzing enzyme, an NSP24 protease, and a fermenting microorganism under suitable fermentation conditions at a temperature below the starch gelatinization temperature of the substrate to produce ethanol, wherein the rate of ethanol production is increased compared to a substantially similar method conducted without the NSP24 protease.

In yet another aspect, the invention relates to a method of producing ethanol in a no cook simultaneous saccharification and fermentation including milled grain substrates comprising adding an NSP24 protease to the simultaneous saccharification and fermentation.

In still a further aspect, the invention relates to a method for decreasing the amount of residual starch produced from the fermentation of granular starch containing substrates comprising fermenting a granular starch containing substrate with a protease, a granular starch hydrolyzing enzyme and a fermenting microorganism, wherein the granular starch containing substrate is not cooked and obtaining a fermented broth wherein the % residual starch in the broth is decreased compared to the amount of residual starch obtained from a substantially similar method without the protease. In some embodiments, the residual starch will be less than 15%. In other embodiments, the protease will be an NSP24 protease.

In yet another aspect, the invention relates to a method for producing an alcohol (e.g. ethanol) comprising pretreating a slurry of a starch substrate at a temperature of about 68° C. to 35° C. for a period of about 30 minutes to 5 hours, fermenting the slurry with a composition comprising yeast, granular starch hydrolyzing enzymes and an NSP24 protease for a period of 12 to 96 hours at a temperature between 10° C. and 50° C. to produce alcohol. In some embodiments, the alcohol is ethanol and in other embodiments the ethanol is recovered from the fermentation. In further embodiments, the pretreatment includes additional enzymes, such as glucoamylase, alpha amylases, proteases or combinations thereof.

BRIEF DESCRIPTION OF THE DRAWINGS

FIG. 1 illustrates the nucleotide sequence of nsp24 (SEQ ID NO: 1) (FIG. 1A) and the predicted amino acid sequence (NSP24, SEQ ID NO: 2) encoded by nsp24 (FIG. 1B), wherein the putative gene intron sequence is identified in bolded format in FIG. 1A and in FIG. 1B the leader sequence is in bold, the prepro sequence is underlined and the mature NSP24 protein sequence, which is represented by SEQ ID NO: 3 starts with KYGAPIS.

FIGS. 2A-D illustrate the nucleotide sequence (SEQ ID NO: 4) of the pTrex3g_NSP24 cDNA clone obtained from *Trichoderma reesei*. The NSP24 gene sequence is underlined and the putative gene intron sequence is identified in bolded format.

DETAIL DESCRIPTION OF THE INVENTION

Figure 3:
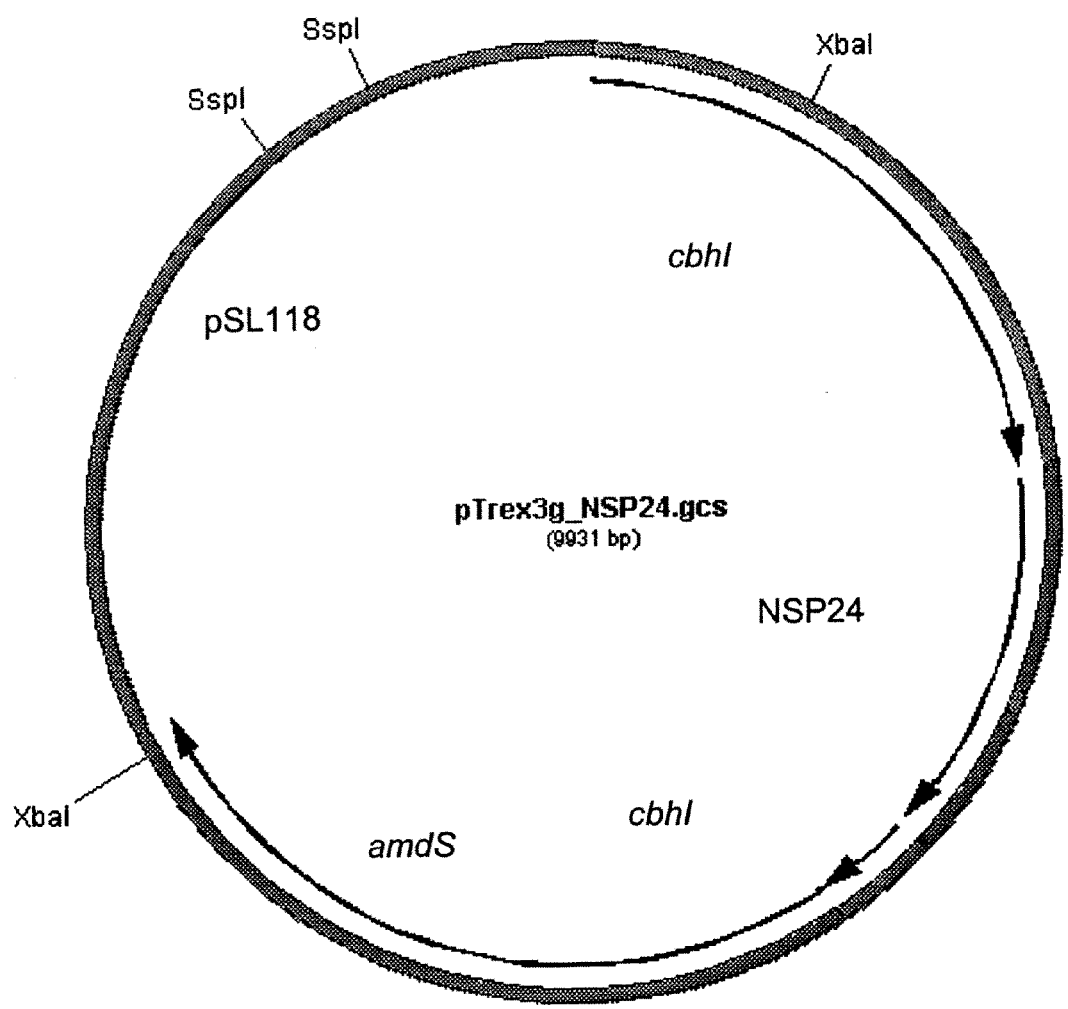
FIG. 3 illustrates the pTrex3g_NSP24 vector and locations of restriction enzyme cleavage sites along the nucleotide sequence of FIG. 2.
Figure 4:
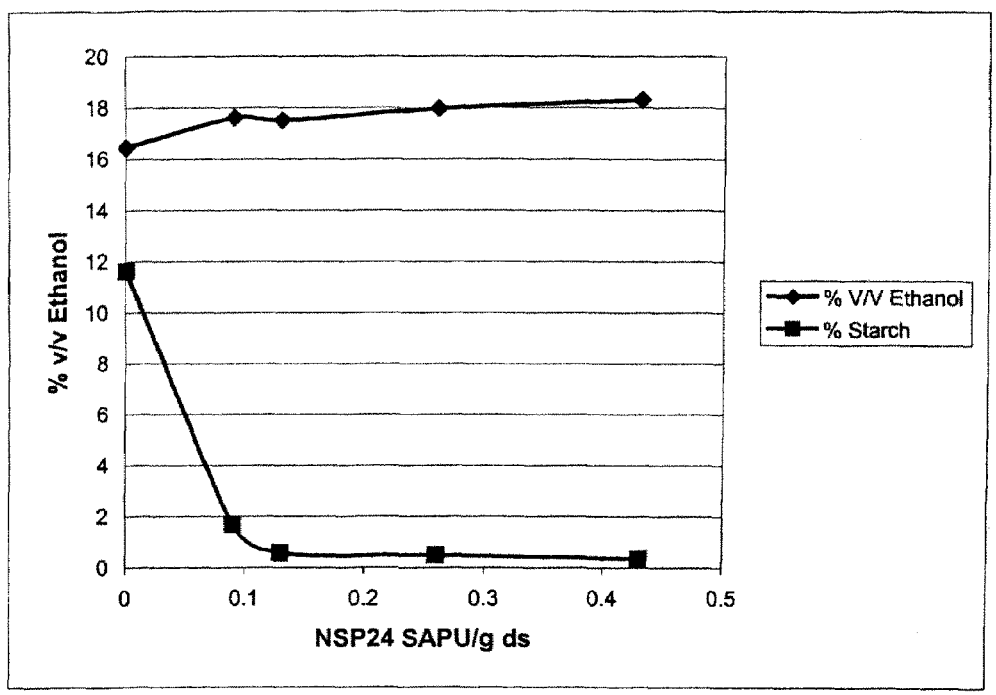
FIG. 4 illustrates the effect of different levels of NSP24 protease on % ethanol (v/v) production during no cook fermentation conditions with degermed ground corn.

The invention will now be described in detail by way of reference only using the following definitions and examples. All patents and publications, including all sequences disclosed within such patents and publications, referred to herein are expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); Kriegler, *Gene Transfer and Expression: A Laboratory Manual* (1990); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), Also, information regarding methods of preparation, expression, isolation and use of proteases may be obtained by review of U.S. Pat. No. 6,768,001.

Other features and advantages of the invention will be apparent from the following detailed description, and from the claims. Although any methods and materials similar or equivalent to those described herein can be used in the practice or testing of the present invention, the preferred methods and materials are described.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with general dictionaries of many of the terms used in this invention.

The headings provided herein are not limitations of the various aspects or embodiments of the invention, which can be had by reference to the specification as a whole. Accordingly, the terms defined immediately below are more fully defined by reference to the specification as a whole.

Numeric ranges are inclusive of the numbers defining the range.

Unless otherwise indicated, nucleic acids are written left to right in 5' to 3' orientation; amino acid sequences are written left to right in amino to carboxy orientation, respectively.

It should be noted that, as used in this specification and the appended claims, the singular forms "a," "an," and "the" include plural references unless the content clearly dictates otherwise. Thus, for example, reference to a composition comprising "a compound" includes a mixture of two or more compounds. It should also be noted that the term "or" is generally employed in its sense including "and/or" unless the content clearly dictates otherwise.

Definitions

"Protease" means a protein or polypeptide domain of a protein or polypeptide derived from a microorganism, e.g. a fungus, bacterium, or from a plant or animal, that has the ability to catalyze cleavage of peptide bonds at one or more of various positions of a protein backbone (e.g. E.C. 3.4).

An "acid protease" refers to a protease having the ability to hydrolyze proteins under acid conditions.

As used herein, "an NSP24 protease" means an enzyme having protease activity and having at least 85% identity with the sequence of SEQ ID NO: 2 or biologically active fragments thereof. The term "NSP24" means the protease having SEQ ID NO: 2 or SEQ ID NO: 3.

A "biologically active fragment" (e.g., a biologically active fragment of NSP24) means a polypeptide fragment having protease activity and one or more amino acid residues deleted from the amino and/or carboxyl terminus of an NSP24 protease sequence.

The term "isolated" or "purified" refers to a protease that is altered from its natural state by virtue of separating the protease from one or more or all of the naturally occurring constituents with which it is associated in nature.

The terms "peptides", "proteins", and "polypeptides" are used interchangeably herein.

As used herein, "percent (%) sequence identity" with respect to the amino acid or nucleotides sequences identified is defined as the percentage of amino acid residues or nucleotides in a candidate sequence that are identical with the amino acid residues or nucleotides in a sequence of interest, after aligning the sequences and introducing gaps, if necessary, to achieve the maximum percent sequence identity, and not considering any conservative substitutions as part of the sequence identity.

As used herein the term "granular starch hydrolyzing enzyme composition" or "granular starch hydrolyzing enzyme" means an enzyme composition capable of hydrolyzing starch in granular form. The compositions may consist of one enzyme or a combination of enzymes.

As used herein the term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

As used herein the term "glucoamylase" refers to the amyloglucosidase class of enzymes (e.g., E.C. 3.2.1.3, glucoamylase, 1,4-alpha-D-glucan glucohydrolase). These are exo-acting enzymes, which release glucosyl residues from the non-reducing ends of amylose and amylopectin molecules. The enzyme also hydrolyzes alpha-1, 6 and alpha-1,3 linkages although at a much slower rate than alpha-1,4 linkages.

As used herein "GAU" refers to a glucoamylase unit, which is the amount of enzyme that will produce 1 g of reducing sugar calculated as glucose per hour from a soluble starch substrate at pH 4.2 and 60° C.

As used herein "SAPU" refers a spectrophotometric acid protease unit, wherein 1 SAPU is the amount of protease enzyme activity that liberates one micromole of tyrosine per minute from a casein substrate under conditions of the assay.

As used herein "SSU" refers to soluble starch unit, 1 SSU is equivalent to the reducing power of 1 mg glucose released per minute at specific incubation conditions.

As used herein "starch" refers to any material comprised of the complex polysaccharide carbohydrates of plants comprised of amylose and amylopectin with the formula $(C_6H_{10}O_5)_X$, wherein X can be any number.

The term "insoluble starch" and "granular starch" are used interchangeably herein and refer to uncooked (raw) starch (e.g. starch that has not been subject to gelatinization).

As used herein the term "gelatinization" means solubilization of a starch molecule by cooking to form a viscous suspension.

The term "residual starch" refers to the remaining starch (soluble or insoluble) left in a fermentation broth after fermentation of a starch containing substrate.

The term "gelatinization temperature" refers to the temperature at which gelatinization begins. The exact temperature of gelatinization depends on the substrate and may vary depending on factors such as plant species and environmental and growth factors.

The phrase "below the gelatinization temperature" refers to a temperature that is less than the temperature that starts gelatinization.

As used herein the term "liquefaction" refers to the stage in starch conversion in which gelatinized starch is hydrolyzed to give low molecular weight soluble dextrins.

As used herein the term "saccharification" refers to enzymatic conversion of starch to glucose.

As used herein the term "soluble starch" or "soluble starch hydrolyzate" refers to soluble products resulting from starch hydrolysis, which may comprise mono-, di-, and oligosaccharides (e.g. glucose, maltose and higher sugars).

The term "milling" refers to the breakdown of substrates comprising starch (e.g. cereal grains) to smaller particles. In some embodiments, the term is used interchangeably with grinding.

The term "fractionated grain" refers to plant grains that include only a portion of the grain.

The term end-product refers to any carbon source derived molecular product which is enzymatically converted from a starch substrate.

The term "enzymatic conversion" refers to the modification of a substrate by enzyme action.

The term polysaccharide" means a compound having multiple monosaccharide units joined in a linear or branched chain. In some embodiments, the term refers to long chains with hundreds or thousands of monosaccharide units. Typical examples of polysaccharides are starch, cellulose and glycogen.

The term "monosaccharide" means a monomeric unit of a polymer such as starch wherein the degree of polymerization (DP) is 1 (e.g., glucose, mannose, fructose and galactose).

The term "disaccharide" means a compound that comprises two covalently linked monosaccharide units (DP2) (e.g., sucrose, lactose and maltose).

The term "DP3+" means polymers with a degree of polymerization greater than 3.

The term "oligosaccharide" means a compound having 2 to 10 monosaccharide units joined in glycosidic linkages.

The term "dry solids content (DS or ds)" refers to the total solids of a slurry in % on a dry weight basis.

The terms "distillers dried grain (DDG)" and "distillers dried grain with solubles (DDGS)" refer to useful co-products of grain fermentation processes.

The term "promoter" means a regulatory sequence involved in binding RNA polymerase to initiate transcription of a gene.

A "heterologous promoter", as used herein is a promoter, which is not naturally associated with a gene or a purified nucleic acid.

A "purified preparation" or a "substantially pure preparation" of a polypeptide, as used herein, means a polypeptide that has been separated from other proteins, lipids, and nucleic acids with which it naturally occurs.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "substantially pure nucleic acid", e.g., a substantially pure DNA, is a nucleic acid which is one or both of: not immediately contiguous with either one or both of the sequences, e.g., coding sequences, with which it is immediately contiguous (e.g., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional NSP24 protease sequence.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein the term "vector" refers to a polynucleotide sequence designed to introduce nucleic acids into one or more cell types. Vectors include cloning vectors, expression vectors, shuttle vectors, plasmids, phage particles, cassettes and the like.

As used herein, "expression vector" means a DNA construct including a DNA sequence which is operably linked to a suitable control sequence capable of affecting the expression of the DNA in a suitable host.

The term "expression" means the process by which a polypeptide is produced based on the nucleic acid sequence of a gene.

As used herein, "operably linked" means that a regulatory region, such as a promoter, terminator, secretion signal or enhancer region is attached to or linked to a structural gene and controls the expression of that gene.

As used herein, a substance (e.g. a polynucleotide or protein) "derived from" a microorganism means that the substance is native to the microorganism.

As used herein, "microorganism" refers to a bacterium, a fungus, a virus, a protozoan, and other microbes or microscopic organisms.

As used herein, "host strain" or "host cell" means a suitable host for an expression vector including DNA according to the present invention and includes progeny of said cells.

The term "filamentous fungi" refers to all filamentous forms of the subdivision Eumycotina (See, Alexopoulos, C. J. (1962), INTRODUCTORY MYCOLOGY, Wiley, New York and AINSWORTH AND BISBY DICTIONARY OF THE FUNGI, 9$^{th}$ Ed. (2001) Kirk et al., Eds., CAB International University Press, Cambridge UK). These fungi are characterized by a vegetative mycelium with a cell wall composed of chitin, cellulose, and other complex polysaccharides. The filamentous fingi of the present invention are morphologically, physiologically, and genetically distinct from yeasts. Vegetative growth by filamentous fungi is by hyphal elongation and carbon catabolism is obligatory aerobic.

As used herein, the term "*Trichoderma*" or "*Trichoderma* sp.*" refer to any fungal genus previously or currently classified as *Trichoderma*.

The phrase "simultaneous saccharification and fermentation (SSF)" refers to a process in the production of alcohols in which a microbial organism, such as an ethanol producing microorganism and at least one enzyme such as a granular starch hydrolyzing enzyme are in the same process step.

As used herein "ethanol producing microorganism" refers to a microorganism or cell with the ability to convert a sugar or oligosaccharide to ethanol. Examples of ethanol producing microorganisms include fungal microorganisms such as yeast. A preferred yeast includes strains of *Saccharomyces*, particularly, *S. cerevisiae*.

As used herein the term "culturing" refers to growing a population of microbial cells under suitable conditions in a liquid or solid medium. In one embodiment, culturing refers to fermentative bioconversion of a starch substrate, such as a substrate comprising granular starch, to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

As used herein the term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein the term "heterologous" with reference to a polypeptide or polynucleotide means a polypeptide or polynucleotide that does not naturally occur in a host cell.

The term "overexpression" means the process of expressing a polypeptide in a host cell wherein a polynucleotide has been introduced into the host cell.

NSP24 Proteases and Polynucleotides Encoding the Same—

The invention relates to NSP24 proteases which in some embodiments are acid proteases, such as acid fungal proteases. The NSP24 protease have at least 85%, at least 90%, at least 93%, at least 95%, at least 96%, at least 97%, at least 98% and at least 99% sequence identity to the amino acid sequence of SEQ ID NO: 2 and biologically active fragments thereof.

In some embodiments, the NSP24 protease is a protease having at least 95% sequence identity to SEQ ID NO: 2 and biologically active fragments thereof. In some embodiments, the NSP24 protease is designated NSP24 and has the sequence of SEQ ID NO: 2 or SEQ ID NO: 3, which is a biologically active fragment of SEQ ID NO: 2.

In some embodiments, the NSP24 protease is a biologically active fragment of a protease having at least 90% sequence identity to SEQ ID NO: 2. In some embodiments, biologically active fragments include proteases having at least 250 amino acid residues, at least 300 amino acid residues, at least 350 amino acid residues, at least 375 amino acid residues, and also at least 400 amino acid residues.

In other embodiments, biologically active fragments include at least 60%, at least 70%, at least 80%, at least 85%, at least 90%, at least 93%, at least 95%, at least 97%, at least 98%, at least 99% of a polypeptide sequence having at least 85%, at least 90%, at least 93%, at least 95%, at least 97%, at least 98% and at least 99% sequence identity with the protein sequence of SEQ ID NO: 2. In some embodiments, the NSP24 protease will comprise at least 60%, at least 70%, at least 80%, at least 85%, at least 90%, at least 95% and at least 98% of a polypeptide sequence having at least 95% sequence identity to SEQ ID NO: 2.

In some embodiments, biologically active fragments are fragments that exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Biologically active fragments may be generated by proteolytic cleavage or alternative splicing events.

In some embodiments, a biologically active fragment will comprise at least 20%, at least 30%, at least 40%, at least 50%, at least 60%, at least 70%, at least 80%, at least 90%, at least 95%, and at least 100% of the protease activity of the NSP24 protease having SEQ ID NO: 2. In some preferred embodiments, a fragment possesses at least 40% or at least 90% of the protease activity of the NSP24 protease of SEQ ID NO: 2 in any in vivo or in vitro protease assay.

NSP24 fragments can be generated by methods known to those skilled in the art. The ability of a candidate fragment to exhibit a biological activity of a protease can be assessed by methods known to those skilled in the art as described herein.

The invention also includes protease analogs. The analogs are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., b or amino acids; and cyclic analogs. Analogs can differ from naturally occurring proteases, such as NSP24 having SEQ ID NO: 2 or SEQ ID NO: 3, in amino acid sequence or in ways that do not involve sequence, or both. Non-sequence modifications include in vivo or in vitro chemical derivatization of the proteases encompassed by the invention. Non-sequence modifications include changes in acetylation, methylation, phosphorylation, carboxylation, or glycosylation. The NSP24 proteases of the invention may include conservative amino acid substitutions using L-amino acids, wherein one amino acid is replaced be another biologically similar amino acid. Nonlimiting examples of conservative replacements include Gly/Ala; Val/Ile/Leu; Lys/Arg; Asn/Gln; Glu/Asp; Ser/Cys/Thr; and Phe/Trp/Tyr.

The invention also relates to polynucleotide sequences encoding the NSP24 proteases encompassed by the invention. Some of these polynucleotides include: a) polynucleotides encoding an NSP24 protease having at least 85%, at least 90%, at least 93%, at least 95%, at least 97%, at least 98%, and at least 99% sequence identity to SEQ ID NO: 2 or SEQ ID NO: 3; b) polynucleotides encoding the sequence of SEQ ID NO: 2; c) a polynucleotide having the sequence of SEQ ID NO: 1; d) polynucleotides encoding a biologically active fragment of an NSP24 protease; e) polynucleotides which have at least 80%, at least 85%, at least 90%, at least 95%, at least 97%, at least 98% and at least 99% sequence identity to the sequence of SEQ ID NO: 1; and f) polynucleotides which hybridize to a nucleic acid probe corresponding to the DNA sequence of SEQ ID NO: 1 or a fragment of SEQ ID NO: 1, said fragment having at least 10, 15, 20, 30, 40, 50, 60, 70, 80, 90, 100 or 150 consecutive nucleotides.

Because of the degeneracy of the genetic code, more than one codon may be used to code for a particular amino acid. Therefore different DNA sequences may encode a polypeptide having the same amino acid sequence as the polypeptide of, for example SEQ ID NO: 2. The present invention encompasses polynucleotides which encode the same polypeptide.

A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art for hydridization under low, medium, high and very high stringency conditions (See, e.g., Sambrook (1989) supra, particularly chapters 9 and 11).

Homology or percent identity of sequences may be determined using computer programs. Methods for performing sequence alignments and determining sequence identity are known to the skilled artisan and may be performed without undue experimentation. See, for examples Ausubel et al., (1995) Current Protocols in Molecular Biology, Chap. 19 (Greene Publishing and Wiley-Interscience, NY) and the ALIGN program (Dayhoff (1978) in Atlas of Protein Sequence and Structure 5: Suppl. 3 (National Biomedical Research Foundation, Washington D.C.). A number of algorithms are available for aligning sequences and determining identity (See, Needleman et al., (1970) J. Mol. Biol. 48:443; Smith et al., (1981) Adv. Appl. Math 2:482; Pearson et al., 91988) Proc. Natl. Acad. Sci 85:2444 and BLASTP, BLASTN and BLASTX algorithms). Various computer programs are known to those in the art including but not limited to ALIGN or Megalign (DNASTAR); WU-BLAST-2; GAP; BLAST; BESTFIT (Altschul et al., (1996) Meth. Enzyme 266:460-480); FASTA and TFASTA (GCG Version B, Madison, Wis.) and CLUSTAL (Intelligenetics).

Expression of NSP24 Proteases in Host Cells—

In some embodiments, polynucleotides encoding the NSP24 proteases of the invention will be introduced into host cells. In some embodiments, the polynucleotide encodes a heterologous protease, and in other embodiments, the polynucleotide codes for an endogenous protease which is over-expressed in the host cell. Some preferred host cells include filamentous fungal cells. Non-limiting examples of filamentous fungal host cells include *Trichoderma* spp. (e.g. *T. viride* and *T. reesei*, the asexual morph of *Hypocrea jecorina*, previously classified as *T. longibrachiatum*), *Penicillium* spp., *Humicola* spp. (e.g. *H. insolens* and *H. grisea*), *Aspergillus* spp. (e.g., *A. niger, A. nidulans, A. orzyae*, and *A. awamori*), *Fusarium* spp. (*F. graminum*), *Neurospora* spp., *Hypocrea* spp. and *Mucor* spp. Further, host cells may include *Bacillus* spp (e.g. *B. subtilis, B. licheniformis, B. lentus, B. stearothremophilus* and *B. brevis*) and *Streptomyces* spp. (e.g., *S coelicolor* and *S. lividans* (TK23 and TK21)).

Vectors and DNA constructs comprising polynucleotides encoding an NSP24 protease encompassed by the invention comprise gene promoter sequences for example of filamentous fungi which are typically cloned into intermediate vectors before transformation into host cells, such as *Trichoderma reesei* cells for replication and/or expression. These intermediate vectors are typically prokaryotic vectors, e.g., plasmids, or shuttle vectors.

To obtain high-level expression of a cloned gene, the heterologous gene is preferably positioned about the same distance from the promoter as is in the naturally occurring gene. As is known in the art, however, some variation in this distance can be accommodated without loss of promoter function. Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The practice of the invention is not constrained by the choice of promoter in the genetic construct. However, exemplary promoters are the *Trichoderma reesei* cbh1, cbh2, eg1, eg2, eg3, eg5, xln1 and xln2 promoters. Also promoters from *A. awamori* and *A. niger* glucoamylase genes (glaA) (Nunberg et al., (1984) *Mol. Cell Biol.* 4:2306-2315) and the promoter from *A. nidulans* acetamidase find use in the vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* is cbhI.

In addition to a promoter sequence, the expression cassette should also contain a transcription termination region downstream of the structural gene to provide for efficient termination. The termination region may be obtained from the same gene as the promoter sequence or may be obtained from different genes.

Although any fungal terminator is likely to be functional in the present invention, some preferred terminators include: the terminator from *Aspergillus nidulans* trpC gene (Yelton, M. et al. (1984) PNAS USA 81:1470-1474, Mullaney, E. J. et al. (1985) MGG 199:37-45), a terminator from *Aspergillus awamori* or *Aspergillus niger* glucoamylase genes (Nunberg, J. H. et al. (1984) Mol. Cell Biol. 4:2306, Boel, E. et al. (1984) EMBO J. 3:1581-1585), the terminator from the *Aspergillus oryzae* TAKA amylase gene, and the terminator from the *Mucor miehei* carboxyl protease gene (EPO Publication No. 0 215 594).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Examples of suitable expression and/or integration vectors are provided in Sambrook et al., (1989) supra, Bennett and Lasure (Eds.) More Gene Manipulations in Fungi, (1991) Academic Press pp. 70-76 and pp. 396-428 and articles cited therein; U.S. Pat. No. 5,874,276 and Fungal Genetic Stock Center Catalogue of Strains, (FGSC, www.fgsc.net.).

Useful vectors may be obtained from Promega and Invitrogen. Some specific useful vectors include pBR322, pUC18, pUC100, pDON™201, pENTR™, pGEN®3Z and pGEN®4Z. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC19 and their derivatives, wider host range plasmids, e.g., RP4, phage DNAs e.g., the numerous derivatives of phage .lambda., e.g., NM989, and other DNA phages, e.g., M13 and filamentous single stranded DNA phages, yeast plasmids such as the 2.mu plasmid or derivatives thereof.

In some embodiments, an expression vector includes a selectable marker. Examples of selectable markers include ones which confer antimicrobial resistance. Nutritional markers also find use in the present invention including those markers known in the art as amdS, argB and pyr4. Markers useful for the transformation of *Trichoderma* are known in the art (see, e.g., Finkelstein, chapter 6, in Biotechnology of Filamentous Fungi, Finkelstein et al., EDS Butterworth-Heinemann, Boston Mass. (1992) and Kinghom et al., (1992) Applied Molecular Genetics of Filamentous Fungi, Blackie Academic and Professional, Chapman and Hall, London). In some embodiments, the expression vectors will also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of a host cell, such as a filamentous fungal host cell. However, transformation resulting in the maintenance of a self-replicating extra-chromosomal transformation vector is also contemplated.

Many standard transfection methods can be used to produce bacterial and filamentous fungal (e.g. *Aspergillus* or *Trichoderma*) cell lines that express large quantities of the protease. Some of the published methods for the introduction of DNA constructs into cellulase-producing strains of *Trichoderma* include Lorito, Hayes, DiPietro and Harman, (1993) Curr. Genet. 24: 349-356; Goldman, VanMontagu and Herrera-Estrella, (1990) Curr. Genet. 17:169-174; and Penttila, Nevalainen, Ratto, Salminen and Knowles, (1987) Gene 6: 155-164, also see U.S. Pat. No. 6,022,725; U.S. Pat. No. 6,268,328 and Nevalainen et al., "The Molecular Biology of *Trichoderma* and its Application to the Expression of Both Homologous and Heterologous Genes" in Molecular Industrial Mycology, Eds. Leong and Berka, Marcel Dekker Inc., NY (1992) pp 129-148; for *Aspergillus* include Yelton, Hamer and Timberlake, (1984) Proc. Natl. Acad. Sci. USA 81: 1470-1474, for *Fusarium* include Bajar, Podila and Kolattukudy, (1991) Proc. Natl. Acad. Sci. USA 88: 8202-8212, for *Streptomyces* include Hopwood et al., 1985, Genetic Manipulation of *Streptomyces*: Laboratory Manual, The John Innes Foundation, Norwich, UK and Fernandez-Abalos et al., Microbiol 149:1623-1632 (2003) and for *Bacillus* include Brigidi, DeRossi, Bertarini, Riccardi and Matteuzzi, (1990) FEMS Microbiol. Lett. 55: 135-138).

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the gene. In one embodiment, the invention concerns a method for producing a protease encompassed by the invention (e.g. an NSP24 protease) which comprises introducing into a host cell a polynucleotide comprising a promoter operably linked to a nucleic acid encoding an NSP24 protease, culturing the host cell under suitable culture conditions for the expression and production of the protease, and producing said protease. In some preferred embodiments, the protease is an NSP24 protease having at least 95% sequence identity to SEQ ID NO: 2 or biologically active fragments thereof.

After the expression vector is introduced into the cells, the transfected or transformed cells are cultured under conditions favoring expression of genes under control of protease gene promoter sequences. Large batches of transformed cells can be cultured as described herein. Finally, product is recovered from the culture using standard techniques. Optimal conditions for the production of the proteins will vary with the choice of the host cell, and with the choice of protease protein to be expressed. Such conditions will be easily ascertained by one skilled in the art through routine experimentation or optimization. Assays to determine protease activity that find use in the present invention include, but are not limited to those described in WO 9934011 and U.S. Pat. No. 6,605,458.

The protease protein of interest may be isolated or recovered and may further be purified after expression in a variety of ways known to those skilled in the art depending on what other components are present in the sample. Conventional procedures for recovering a protease from culture medium include separation by centrifugation or filtration, or if necessary, disrupting the cells and removing the supernatant from the cellular fraction and debris. In some cases, after clarification, the proteinaeceous components of the supernatant or filtrate are precipitated by means of a salt, e.g., ammonium sulphate. The precipitated proteins are then solublized and may be purified by a variety of chromatographic procedures. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. For general guidance in suitable purification techniques, see Scopes, Protein Purification (1982).

Cell Cultures—

Host cells and transformed cells can be cultured in conventional nutrient media. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; www.atcc.org). Stable transformants of fungal host cells, such as Trichoderma cells can generally be distinguished from unstable transformants by their faster growth rate or the formation of circular colonies with a smooth rather than ragged outline on solid culture medium. See, for example Davis et al., (1970) Methods Enzymol. 17:79-143).

In some embodiments of the present invention, fungal cells expressing a NSP24 protease according to the invention are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolism repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Methods for the Production of Ethanol and By-Products—

In one embodiment, the invention comprises methods for producing ethanol comprising saccharifying a milled insoluble starch substrate with a granular starch hydrolyzing enzyme composition and a protease at a temperature below the gelatinization temperature of the starch in the substrate. While in general acid proteases, such as proteases derived from fungal strains (e.g. Aspergillus, Mucor, Rhizopus, Trichoderma, Penicillium, and Endothia) may be useful in the methods of the invention, preferred proteases include NSP24 proteases as described above.

An insoluble starch containing substrate may be obtained from any plant material including any plant part containing starch, such as seeds, kernels, grains, leaves, tubers, roots, stems and the like. Particularly preferred plant sources include corn; wheat; rye; sorghum; rice; millet; barley; rice, milo, cassava; legumes, such as beans and peas; sugarcane; potatoes; sweet potatoes; bananas; tapioca and mixtures thereof. Some preferred sources of insoluble starch substrates include corn, wheat, barely, rye and sorghum.

Various references have reported on the amount of starch found in cereal grains and reference is made to The Alcohol Textbook, $3^{rd}$ Ed. K. Jacques et al., Eds. 1999, Nottingham University Press. For example corn contains about 60-68% starch; barley contains about 55-65% starch; millet contains about 75-80% starch; wheat contains about 60-65% starch; and polished rice contains 70-72% starch.

The plant material may be by-products, such as corn fiber, corncobs, stover and other cellulose or hemicellulose containing plant residues and materials. In addition, insoluble starch substrates include fractionated plant material. Typical examples include fractionated corn, sorghum, barley and wheat. Some preferred embodiments include fractionated corn, such as endosperm, germ or fiber (bran) but particularly endosperm for corn and gluten starch for wheat. Those of general skill in the art are well aware of methods available to prepare fractionated grains (See, U.S. Pat. No. 6,254,914, U.S. Pat. No. 6,899,910; U.S. Pat. No. 6,936,294; U.S. Pat. No. 6,936,110 and U.S. Pat. No. 6,408,105; Singh and Johnston (2004) Adv. Food and Nutr. Res. 48:151-171 and Singh et al., (1999) Cereal Chem 76:868-872).

Milling of the insoluble starch substrate may be by either wet milling or dry milling. In some preferred embodiments, the insoluble substrate is dry-milled. In general if the substrate (e.g. grain) is not fractionated the non-fermentable components of the grain (e.g. the fiber, protein and germ) are carried through the fermentation process and are recovered as the by-product, distillers dried grain and distillers dried grain with solubles.

In either wet or dry milling fractionation processes, mechanical grinding followed by density separation is used for the different fractions or corn germ, fiber and endosperm (Ponnampalan et al., (2004) Appl. Biochem. Biotech., 115: 837-842) and Simms L., (1985) "The Technology of Corn Wet Milling" in Starch Conversion Technology, Ed. G. M. A. van Beynnum and J. A. Roels Marcel Dekker Inc., NY).

Dry milling of whole cereal grains is known in the art and includes the use of hammer mills and roller mills. Also dry mill fractionation processes are known (Brekk O. L. (1970) "Corn Dry Milling Industry" pages 262-291 in Corn Culture Products G. E. Inglett Ed., AVI Publishing, Westport Conn.). An example of a typical composition of dry milled whole ground corn (WC) as compared to fractionated corn (FC) is as follows: moisture—13% (WC) and 12% (FC); protein—7.8% (WC) and 7.0% (FC); fat—3.5% (WC) and 0.7% (FC); crude fiber—1.5% (WC) and 0.5% (FC); ash—1.3% (WC) and 0.4% (FC) and carbohydrate—72.9% (WC) and 79.4% (FC) (Duensing et al., Corn Dry Milling: Processes, Products and Applications in Corn: Chemistry and technology ED. White et al. However, with modernization and advancements in the dry fractionation of ground corn, the endosperm fraction may contain greater than 80% starch.

In some embodiments, a milled substrate will be prepared by e.g. grinding wherein at least 50%, at least 55%, at least 60%, at least 65% and at least 70% of the ground particles will pass through a sieve having an aperture size of about 600 micrometers (between 585 and 610) designated herein as a 30 mesh screen. In some embodiments, less than 85%, less than 80%, less than about 75%, less than about 70%, less than about 65%, less than about 60%, less than about 55%, less than about 50%, less than about 45%, or less than about 40% of the ground particles will pass through a 30 mesh screen. In some embodiments, at least 25%, at least 30%, at least 40%, at least 30% and also at least 35% of the milled substrate will be retained on a 30 mesh screen. Also in some embodiments, between 30%-80% of the milled particles will pass through a 30 mesh screen. In other embodiments, between 30%-75%, also between 30%-70%, also between 35%-65%, and also between 40%-60% of the milled particles will pass through a 30 mesh screen.

The insoluble starch substrate in some embodiments is mixed with mashing liquor to form a slurry. The mashing liquor may be water and process water, such as stillage (backset) or a mixture of both. Stillage is the distillation residue of the fermentation and may include sugars, nitrogen and other nutrients and enzymes. Stillage can be used in proportion of 1% to 95%, also in the range of 15% to 75% and about 30% to 60% instead of water.

The % dry solids (DS) of a slurry may be in the range of about 10% to about 55%, in the range of about 15% to about 50%, in the range of about 20% to about 50%, in the range of about 25% to about 50%, in the range of about 30% to about 45%.

Saccharification takes place by contacting a substrate with a granular starch hydrolyzing enzyme composition and an NSP24 protease of the invention as previously described in detail above.

The amount of an NSP24 protease used in the methods of the invention will vary between the range of 0.001 to 10 SAPU/g DS. In some embodiments, the amount of an NSP24 protease will be between the range of 0.01 and 10.0 SAPU/g DS. In other embodiments, the amount of NSP24 protease will be between the range of about 0.05 and 5.0 SAPU/g DS. In other embodiments, the amount of NSP24 protease will range from 0.05 to 5 kg/metric ton (MT). Other useful amounts include the range of from 0.1 to 1 kg/MT NSP24 protease.

Granular starch hydrolyzing enzymes and enzyme compositions are known in the art and include compositions supplying glucoamylases and alpha amylases as separate enzymes or in combinations. The enzymes may be wild type or genetically modified enzymes including variants and hybrids.

Non-limiting examples of glucoamylases having granular starch hydrolyzing activity are glucoamylases derived from *Humicola* (*H. grisea*) (WO 2005/052148; U.S. Pat. No. 4,618,579; Tosi et al., 91993) Can. J. Microbiol. 39:846-852; Campos et al., (1995), App and Environ. Microbiol. 61:2436-2438; EP 171218; and Allison et al., (1992) Cur. Genet 21:225-229); *Aspergillus* (*A. niger A, awamori*, and *A. kawachi*) (Ueda et al., (1981) Biotechnology. Bioeng 23: 291, Hayashida (1973) Agr. Biol. Chem. 39:2093-2099 and Hayashida et al., (1980) Agric. Biol. Chem. 53:923-929); *Trichoderma* (*T. reesei*); and *Rhizopus* (*R. niveus* and *R. oryzae*) (U.S. Pat. No. 4,514,496, U.S. Pat. No. 4,092,434, U.S. Pat. No. 4,863,864; Takahashi et al., J. Biochem. (1985) 98: 663-671 and Ashikari et al., (1986) Agric. Biol. Chem. 50:957 964). Non-limiting examples of alpha amylases having granular starch hydrolyzing activity are derived from *Aspergillus* (*A. kawachi*) (See, US Appln. 2005/0266543 and Ueda et al., (1980) J. Fermentation Technol. 58:237-242). Recently a number of patent applications have been published which are directed to various enzyme compositions, which include granular starch hydrolyzing activities and the use of these compositions in alcohol fermentations. These publications include for example WO 03/066826; WO 04/113551; WO 04/081193; WO 04/106533; WO 05/052148 and WO 05/087938. Some of the enzymes disclosed as having granular starch hydrolyzing activity include wild type enzyme and variants and hybrids thereof.

Commercially available granular starch hydrolyzing compositions are available from Genencor International Inc. (Danisco A/S), STARGEN001; Shin Nihon Chemical Co. Japan, CU CONC; Bicon, India LTD., Bangalore, India M1 Amano and Novozymes A/S.

While the saccharifying step of the invention includes a granular starch hydrolyzing enzyme and an NSP24 protease, additional enzymes may be added to the mixture, such enzymes include for example other glucoamylases and amylases.

The amount of glucoamylase employed in the present process can vary according to enzyme activity. In some embodiments, suitable amounts include 0.01 to 15 GAU/g DS and also 0.01 to 10.0 GAU/g ds. Also a useful amount of glucoamylase in a granular starch hydrolyzing composition is about 0.1 to 5 GAU/g DS, also about 0.2 to 1.5 GAU/g DS.

The temperature of the saccharification will be conducted at a temperature below the temperature of gelatinization of the substrates. The exact temperature used in accordance with the methods of the invention depends upon the specific starch substrate used. General starch gelatinization temperature ranges are disclosed in Swinkels pages 32-38 in STARCH CONVERSION TECHNOLOGY, eds Van Beynum et al., (1985) Marcel Dekker Inc., NY and THE ALCOHOL TEXTBOOK, A REFERENCE FOR THE BEVERAGE, FUEL AND INDUSTRIAL ALCOHOL INDUSTRIES, $3^{rd}$ Ed., eds Jacques et al., 1999, Nottingham University Press, UK. In some embodiments, the methods according to the invention will be conducted at a temperature of at least about 10° C., 15° C., 20° C., 25° C., 30° C., 35° C., 40° C., 45° C., 50° C., 55° C., 60° C., and 65° C. In other embodiments, the temperature will be between about 10-65° C., between about 20-60° C., between about 30-65° C., between about 35-65° C., between about 40-65° C., and between about 45-65° C. In other embodiments, the temperature will be between about 10-45° C., between about 20-45° C., between about 25-40° C., between about 30-40° C. and between about 30-35° C. In some preferred embodiments, the starch substrate is never subjected to the thermal conditions used for liquefactions and generally will be below 68° C. The temperature may vary during the saccharification process but the temperature will always be maintained at a temperature below the temperature of gelatinization for the substrate(s) used in the process.

In some embodiments, the methods according to the invention will be conducted at a pH of about pH 3.0 to 6.5; about pH 3.0 to 6.0; about pH 3.5 to 5.5, about pH 3.5 to 5.0; and about pH 3.5 to 4.5. In addition the pH during this step may vary. For example the pH may be increased during the saccharification. For example the pH may be increased from a pH of about 3 to 5.0 to a pH of about 4 to 6.

In some embodiments, the residence time of the method is from about 2 to 300 hrs, but more typically from 2 to 120 hours. In some embodiments, the process is conducted from about 5 to 100 hours. In other embodiments, the process is conducted from about 5 to 80 hours. In still other embodiments, the process is conducted for at least 5 hours but less than 100 hours.

In some embodiments, at least 60%, 65%, 70%, 75%, 80%, 85%, 90%, 94%, 95%, 96%, 97%, 98% and 99% of the dry solids of the insoluble starch is hydrolyzed. In some embodiments, the insoluble starch substrate is completely hydrolyzed. In some embodiments, at least 90% of the granular starch is hydrolyzed in 100 hours. In certain embodiments, at least 90% of the granular starch substrate is hydrolyzed in a time period of 24 hours. In other embodiments, at least 95% of the granular starch substrate is hydrolyzed in a time period of 24 hours.

In some embodiments, the saccharification step is followed by fermentation. The saccharified mash is contacted with a fermenting organism under suitable fermentation conditions. In some preferred embodiments, the fermenting organism is a commercially available yeast, such as a strain of *Saccharomyces cerevisiae* (U.S. Pat. No. 4,316,956). Commercial sources of yeast include FALI; RED STAR (Red Star); RED STAR RED (Red Star); FERMIOL (DSM Specialties) and SUPERSTART (Alltech). The amount of starter yeast employed in the methods is an amount effective to produce a commercially significant amount of ethanol in a suitable amount of time, (e.g. to produce at least 15% ethanol from an insoluble corn substrate having between 25-40% DS in less than 72 hours). The use of yeast in fermentation is well known and reference is made to THE ALCOHOL TEXTBOOK, K. JACQUES ET AL., EDS. 1999, NOTTINGHAM UNIVERSITY PRESS, UK.

The fermentation may be conducted under the same conditions of temperature, pH and the like as described above for saccharification.

In some preferred embodiments, the method comprises a simultaneous saccharification and fermentation (SSF), wherein the saccharification step and fermentation step are carried out contemporaneously. The culture medium, which includes the insoluble starch substrate contacted with a granular starch hydrolyzing composition and NSP24 protease either supplied in a cell free filtrate or expressed from a fungal host cell in the culture, will also include fermenting organism such as yeast.

In some embodiments, the residence time for the simultaneous saccharification and fermentation will be from about 2 to 300 hours, but preferably from 2 to 120 hours. In some embodiments, the time is from about 5 to 100 hours. In other embodiments, the time is from about 5 to 80 hours. In still other embodiments, the time is for at least 5 hours but less than 100 hours. In other embodiments, the process time is for at least about 10 hours but less 100 hours at a temperature between 20-50° C. and preferably between 25-40° C. and a pH of 3.5 to 6.0.

In some embodiments at least 5 vol %, at least 8 vol %, at least 10 vol %, at least 12 vol %, at least 15 vol %, at least 18 vol % and at least 20 vol % of ethanol will be produced in the fermentation media. In other embodiments, the amount of ethanol produced in the fermentation media (broth) will be between 5-30% (v/v), also between 5-25% (v/v), and between 5-20% (v/v). In some embodiments, the amount of ethanol produced will be at least 16% in 72 hours.

In some embodiments the amount of ethanol produced is enhanced compared to the amount of ethanol produced from a substantially similar method, which does not include an NSP24 protease. The ethanol production from the fermentations encompassed by the methods of the invention may be increased by at least 0.5%, at least 0.75%, at least 1.0%, at least 1.25%. at least 1.5%, at least 1.75% and at least 2.0% over a substantially similar method. A substantially similar method means a method conducted under the same conditions of temperature, pH, residence time, fermenting organism, granular starch hydrolyzing enzymes and the like. The only essential difference being the inclusion of the protease and specifically NSP24 protease in the saccharifying/fermenting media.

Following fermentation, alcohol (e.g., ethanol) may be recovered from the fermentation media by means well known in the art. In some embodiments, the alcohol in the fermented medium may be distilled, for example by heating or vacuum distillation. Reference is made to THE ALCOHOL TEXTBOOK, A REFERENCE FOR THE BEVERAGE, FUEL AND INDUSTRIAL ALCOHOL INDUSTRIES $3^{RD}$ ED., K. JACQUES ET AL., EDS. 1999, NOTTINGHAM UNIVERSITY PRESS, UK.

The ethanol may then be used, for example, as fuel ethanol or potable ethanol. The remaining residue, known as stillage may also be recovered and components of the stillage recycled for the next fermentation or the stillage may be separated into a soluble fraction or insoluble fraction.

When the stillage is separated for example by centrifugation or screening into a soluble fraction and an insoluble fraction, these fractions can be used to make distillers' solubles or distillers' dried solubles or mixed together to make distillers' dried grain plus solubles (DDGS). One skilled in the art is familiar with processes for forming DDGS and distillers' grains in general. In some embodiments of the invention, when % ethanol increases in the fermentation process, the amount of DDGS decreases. In some embodiments the % residual starch at the end of the fermentation may decrease even without significant increase in ethanol production. In one embodiment, an advantage of the method encompassed by the invention may be an increase in the % total protein in the DDGS. The DDGS may then be used for example, in an animal feed formulation.

In another embodiment, an advantage of including a protease in the methods encompassed by the invention is a decrease in the residual starch in a yeast fermentation of granular starch containing substrates such as a milled whole grain or fractionated grain. High levels of residual starch in a fermentation media (broth) from yeast fermentation using granular starch containing substrates may potentially result in problems in the distillation step, which could cause poor separation of insoluble solids from solubles during centrifugation. In addition, high levels of residual starch could potentially cause higher viscosity. In some embodiments of the invention, the addition of a protease, preferably an NSP24 protease (e.g. NSP24), during yeast fermentation of a granular starch containing substrate (e.g. a grain such as fractionated or whole corn) results in a reduction of the residual starch in the fermentation broth. The fermentation broth may then be used advantageously for further processing.

In some embodiments, the fermentation process (e.g. SSF) encompassed by the invention will result in byproducts (e.g. DDGS) containing less than 30%, less than 15%, less than 10%, less than 9%, less than 8%, less than 7%, less than 6%, less than 5%, less than 4%, less than 2% and less than 1% residual starch. In some embodiments, the amount of residual starch produced by the methods of the invention after 72 hours will be less than 15%, less than 12%, less than 10%, less than 8% and less than 5%. In some embodiments of the invention, the amount of residual starch produced by the methods of the invention will be at least about 50%, at least about 40%, at least about 30%, at least about 25%, at least about 20%, at least about 15%, at least about 10%, at least about 5.0%, at least about 3.0%, and at least about 2.0% less than a substantially similar method conducted without a protease and particularly an NSP24 protease.

In another embodiment, the insoluble (granular) starch substrate may be pretreated prior to saccharification. Pretreatment may include exposing the insoluble starch substrate preferably in slurry form to an elevated temperature, wherein the temperature is below the starch gelatinization temperature of the starch substrate.

In some embodiments, the heat pretreatment may be at a temperature of below 68° C. but above 40° C. In some embodiments, the pretreatment will be between 40-65° C., also between 40-60° C., also between 45-55° C. and between 42-52° C., at a pH range of 3.0 to 6.0, also between pH 3.0 and 5.5, also between a pH of 3.5 to 5.5, also between pH of 3.5 to 5.0 and also between pH 3.8 to 4.5. In some embodiments, when corn is the substrate the pretreatment will be conducted at about 55 to 65° C. and at a pH of about 3.5 to 4.2. In other embodiments, when rye is the substrate the pretreatment will be conducted at about 40 to 50° C.

In some embodiments, the pretreatment will be conducted for 15 minutes to 24 hours, also from 30 minutes to 18 hours, also from 30 minutes to 12 hours, also from 30 minutes to 8 hours and also from 1 hour to less than 4 hours.

In addition to the heat pretreatment, different enzymes may be included in the pretreatment. In some embodiments, the pretreatment will include the use of an alpha amylase, such as bacterial alpha amylase (e.g., SPEZYME and GZYME 997 (Genencor International, Inc.)) and optionally a cellulase (e.g. Cellulase 2000). In other pretreatment embodiments, the enzyme may include granular starch hydrolyzing enzymes (e.g. alpha amylase derived from *Aspergillus kawachi* or granular hydrolyzing glucoamylase derived from *Humicola grisea*)).

In some embodiments, the pretreatment may include an acid protease, such as an NSP24 protease encompassed by the present invention. However, other acid proteases may be used including GC106 (Genencor International). In some embodiments, the amount of an acid protease used in a pretreatment will be in the range of 0.05 to 15 SAPU/g DS, also the dosage of 0.1 to 10 SAPU/g DS; 0.1 to 5 SAPU/g DS; and 0.25 to 5 SAPU/g DS find use in the invention. In some preferred embodiments, 0.5 to 2.0 SAPU/g DS and even 0.5 to 1.0 SAPU/g DS of an NSP24 protease will find use in the pretreatments of the invention. In some embodiments, the pretreatment may increase the amount of ethanol that is produced by the fermentation of the insoluble substrates as compared to the amount of ethanol produced by the fermentation of the insoluble substrate without a pretreatment but under substantially similar conditions. In some embodiments, the amount of ethanol will be increase by at least 0.3%, at least 0.5%, at least 0.75% or even at least 1.0%. In some embodiments, the amount of residual starch will be decreased by at least 1%, at least 2% at least 3%, a least 4%, at last 5%, at least 6%, at least 7%, at least 8%, at least 9%, at least 10% compared to the % of residual starch in a substantially similar fermentation without the pretreatment.

Additional enzymes may be added to the fermentations described above. These enzymes may be wild type enzymes, hybrids or variants of wild type enzymes including glucoamylases; alpha amylases; pullulanases; cellulases, such as endoglucanases; hemicellulases, such as mannases; lipases (e.g. E.C. 3.1.1.3); glucose oxidases; pectinases; xylanases; cutinases (e.g. E.C. 3.1.1.74); transglucosidases; transferases and alpha 1,6, glucosidases (e.g., E.C. 3.2.1.20). Some preferred glucoamylases useful in the methods of the invention are produced by several strains of filamentous fungi and yeast. In particular, glucoamylases secreted from strains of *Aspergillus* and *Trichoderma* are commercially important. Sources of these glucoamylases include: *Aspergillus niger* G1 and G2 glucoamylase and variants thereof (Boel et al., (1984) *EMBO J.* 3:1097-1102; WO 92/00381; WO 00/04136 and U.S. Pat. No. 6,352,851); *Aspergillus awamori* glucoamylases (WO 84/02921); *Aspergillus oryzae* glucoamylases and variants thereof (Hata et al., (1991) *Agric. Biol. Chem.* 55:941-949) and *Aspergillus shirousami* (See Chen et al., (1996) *Prot. Eng.* 9:499-505; Chen et al. (1995) *Prot. Eng.* 8:575-582; and Chen et al., (1994) *Biochem J.* 302:275-281). Glucoamylases are also obtained from strains of *Talaromyces* such as those derived from *T. emersonii, T. leycettanus, T. duponti* and *T. thermophilus* (WO 99/28488; U.S. Pat. No. RE: 32,153; and U.S. Pat. No. 4,587,215); strains of *Rhizopus*, such as *R. niveus* and *R. oryzae*; strains of *Mucor*; strains of *Trichoderma*, such as *T. reesei* and *T. viride*, strains of *Humicola*, such as *H. grisea* (See, Boel et al., (1984) *EMBO J.* 3:1097-1102; WO 92/00381; WO 00/04136; Chen et al., (1996) *Prot. Eng.* 9:499-505; Taylor et al., (1978) *Carbohydrate Res.* 61:301-308; U.S. Pat. No. 4,514,496; U.S. Pat. No. 4,092,434; and Jensen et al., (1988) *Can. J. Microbiol.*

34:218-223), and glucoamylase obtained from *Athelia rolfsii* and variants thereof (WO 04/111218).

Other additional enzymes, which find use in the present invention, include debranching enzymes such as pullulanases (E.C. 3.2.1.41) and isoamylases (E.C. 3.2.1.68). Such enzymes hydrolyze alpha-1,6-glucosidic bonds. Thus, during the hydrolysis of the starch, debranching enzymes remove successive glucose units from the non-reducing ends of the starch. Another enzyme that may be used in the methods of the invention are beta-amylases (E.C. 3.2.1.2). These are exo-acting maltogenic amylases, which catalyze the hydrolysis of 1,4-alpha-glucosidic linkages in amylose, amylopectin and related glucose polymers. Some of these enzymes are characterized as having an optimum pH range from 4.5 to 7.0 and optimum temperature range from 40° C. to 65° C. Commercial beta-amylases are available for example SPEZYME BBA and OPTIMALT from Genencor International Inc.

Additional enzymes may include alpha amylases, which may or may not be characterized by having granular starch hydrolyzing activity. Examples of alpha amylases include both bacterial and fungal alpha amylases and variants thereof, such as alpha amylases from *Bacillus amyloliquefaciens, Bacillus stearothermophilus, B. licheniformis* and variants or hybrids thereof (U.S. Pat. No. 5,093,257; U.S. Pat. No. 6,093,562; U.S. Pat. No. 5,736,499; U.S. Pat. No. 5,958,739; U.S. Pat. No. 6,436,888; U.S. Pat. No. 6,867,031; WO 96/39528; WO 96/23874 and WO 05/001064). Commercially available alpha amylases are SPEZYME FRED and SPEZYME ETHYL (Genencor International Inc.). Cyclodextrin glucanotransferases (CGTases) (E.C. 2.4.1.19) and variants thereof may also find use in the invention (U.S. Pat. No. 5,278,059; U.S. Pat. No. 5,545,587 and WO 05/003337).

The effective amount of these enzymes to be included in the methods of the invention can be readily determined by one skilled in the art.

In some embodiments, an antimicrobial may be added to the compositions and fermentation medium of the invention. Antimicrobials are compounds that kill or inhibit the growth of microorganisms.

Material and Methods

In the experimental section that follows, the following abbreviations apply: NSP24 (NSP24 of the invention which is overexpressed in *Trichoderma reesei*; AnGA (DISTILLASE comprising an *Aspergillus niger* GA (Genencor International Inc.,)); GA (glucoamylase); TrGA (a GA obtained from *Trichoderma reesei*); STARGEN 001 (a granular hydrolyzing enzyme composition including glucoamylase and alpha amylase activity (Genencor International Inc.,)); AkAA (an *Aspergillus kawachi* alpha amylase) GAU (glucoamylase unit); SAPU (spectrophotometric acid protease unit) wt % (weight percent); ° C. (degrees Centigrade); rpm (revolutions per minute); $H_2O$ (water); $dH_2O$ (deionized water); $dIH_2O$ (deionized water, Milli-Q filtration); aa or AA (amino acid); bp (base pair); kb (kilobase pair); kD or kDa (kilodaltons); g or gm (grams); μg (micrograms); mg (milligrams); μL (microliters); ml and mL (milliliters); mm (millimeters); μm (micrometer); M (molar); mM (millimolar); μM (micromolar); U (units); V (volts); MW (molecular weight); sec (seconds); min(s) (minute/minutes); hr(s) (hour/hours); DO (dissolved oxygen); kg (kilogram); MT (Metric ton) and EtOH (ethanol).

The following assays and methods are used in the examples provided below:

Ethanol and Carbohydrate Determinations

Ethanol and carbohydrate composition of the samples were determined using the HPLC method as described herein:

a) a 1.5 mL Eppendorf centrifuge tube was filled with fermentor beer and cooled on ice for 10 min;

b) the sample tube was centrifuged for 1 min in Eppendorf table top centrifuge;

c) a 0.5 mL sample of the supernatant was transferred to a test tube containing 0.05 mL of Kill solution (1.11N $H_2SO_4$) and allowed to stand for 5 min;

d) 5.0 mL of water is added to the test tube sample and then filtered into a HPLC vial through 0.45 μm Nylon Syringe Filter; and e) run on HPLC.

HPLC Conditions:

a) Ethanol System: Column: Phenomenex Rezex Organic Acid Column (RHM-Monosaccharide) #00H 0132-KO (Equivalent to Bio-Rad 87H); Column Temperature: 60° C.; Mobile Phase: 0.01 N $H_2SO_4$; Flow Rate: 0.6 mL/min; Detector: RI; and Injection Volume: 20 μL.

b) Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min; Detector: RI; Injection Volume: 10 μL (3% DS material)

The column separates based on the molecular weight of the saccharides, which are designated as DP-1 (monosaccharides); DP-2 (disaccharides); DP-3 (trisaccharides) and DP>3 (oligosaccharide sugars having a degree of polymerization greater than 3).

Residual starch iodine test: A sample of the beer (fermentation broth) was centrifuged in 2 ml plastic centrifuge tubes. The supernatant was decanted and the tube containing the pellet was placed in an ice bath. Several drops of 0.025N iodine solution (0.1N iodine from VWR Cat. No. VW3207-1 diluted 4x) was added to the pellet and mixed. A positive (+) starch shows a range of color from blue to purple and the intensity of color is directly proportional to the concentration of starch. A negative result (−) remains yellowish.

Determination of total starch content: The enzyme-enzyme starch liquefaction and saccharification process (dual enzyme method) was used to determine the total starch content. In a typical analysis, 2 g of the dry sample was taken in a 100 ml Kohlraucsh flask and 45 ml of MOPS buffer, pH 7.0 was added. The slurry was well stirred for 30 min. SPEZYME™ FRED (1:50 diluted in water), 1.0 ml was added and heated to boiling for 3-5 min. The flask was placed in an autoclave maintained at 121° C. for 15 min. After autoclaving the flask was placed in a water bath at 95° C. and 1 ml of 1:50 diluted SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX™ L-400 (Glucoamylase, Genencor International Inc.) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

Total protein analysis: The total nitrogen (N) in the sample preparations was determined using the Kjeldhal method (American Assoc. Cereal Chemists (AACC), (1983), Methods 22B60 8th Ed. St Paul, Minn.). Protein content was calculated by 6.25× total N.

EXAMPLES

The following examples are provided in order to demonstrate and further illustrate certain preferred embodiments and aspect of the present invention and are not to be construed as limiting the scope thereof.

Example 1

Cloning of Protease, NSP24 and Transformation into *Trichoderma reesei*

Genomic DNA was extracted from *T. reesei* strain QM6a. PCR primers were designed, based on the putative protease sequence found in contig 1-5500 of the *T. reesei* genome (Joint Genome Institute (JGI) *T. reesei* genome v1.0). The forward primer contained a motif for directional cloning into the pENTR/D vector (Invitrogen).

The sequence of the afp6f primer was CACCATGCAGACCTTTGGAGCT (SEQ ID NO: 5), and the sequence of the afp7r primer was TTATTTCTGAGCCCAGCCCAG (SEQ ID NO: 6). The 1.3 kb PCR product was purified by gel extraction (Gel Purification kit, Qiagen) and cloned into pENTR/D, according to the Invitrogen Gateway system protocol.

The vector was then transformed into chemically competent Top10 *E. coli* (Invitrogen) with kanamycin selection. Plasmid DNA, from several independent clones, was digested with restriction enzymes to confirm the correct size insert. The protease gene insert was sequenced (Sequetech, Mountain View, Calif.) from several clones. Plasmid DNA from one clone, pENTR/D_55.3, was added to the LR clonase reaction (Invitrogen Gateway system) with pTrex3g/amdS destination vector DNA. The pTrex3g vector is based on the *E. coli* pSL1180 (Pharmacia Inc., NJ), which is a pUC118 phagemid based vector and is described in WO 05/001036. Recombination, in the LR clonase reaction, replaced the CmR and ccdB genes of the destination vector with the *T. reesei* protease from pENTR/D_55.3. This recombination directionally inserted protease between the cbhI promoter and terminator of the destination vector. Recombination site sequences of 44 and 50 bp remained upstream and downstream, respectively, of the protease gene. An aliquot of the LR clonase reaction was transformed into chemically competent Top10 *E. coli* and grown overnight with carbenicillin selection. Plasmid DNA from several clones was digested with restriction enzymes to confirm the correct insert size. Plasmid DNA from clone, pTrex3g_55.3.1 was digested with XbaI to release the expression cassette including the cbhI promoter: NSP24 protease:terminator:amdS. This 5.8 kb cassette was purified by agarose gel extraction, using standard techniques, and transformed into a strain of *T. reesei* derived from the publicly available strain QM6a (See, WO 05/001036). Reference is made to FIGS. 1, 2 and 3.

A 2 cm² agar plug from a plate of sporulated mycelia was inoculated into 50 ml of YEG broth in a 250 ml, 4-baffled shake flask and incubated at 37° C. for 16-20 hours at 200 rpm. The mycelia were recovered by transferring liquid volume into 50 ml conical tubes and spun at 2500 rpm for 10 minutes. The supernatant was aspirated off. The mycelial pellet was transferred into a 250 ml, 0.22 μm CA Corning filter bottle containing 40 ml of filter-sterilized β-D-glucanase (InterSpex Products, Inc.) solution and incubated at 30° C., 200 rpm for 2 hours. The mycelia were harvested through sterile Miracloth (CalBiochem, LaJolla, Calif.) into a 50 ml conical centrifuge tube, centrifuged at 2000 rpm for 5 minutes, aspirated. The pellet was washed once with 50 ml of 1.2M sorbitol, centrifuged again, aspirated, and washed with 25 ml of sorbitol/CaCl$_2$. The protoplasts were counted using a hemocytometer, centrifuged, aspirated, and resuspended in a volume of sorbitol/CaCl$_2$ sufficient to generate a protoplast concentration of 1.25×10$^8$/ml. Aliquots of 200 μl were used per transformation reaction. 20 μg of DNA (>1 μg/ul) was placed into 15 ml conical tubes and the tubes were placed on ice. 200 μl of the protoplasts were added. 50 μl PEG mix was added and mixed gently and incubated on ice for 20 minutes. 2 ml of PEG mix was added to the tubes and incubated at room temperature for 5 minutes. 4 ml sorbitol/CaCl$_2$ (for a total of 6.25 ml) was added to the tubes. This transformation mixture was divided into 3 aliquots of ~2 ml per each overlay. The 2 ml was added to a tube of melted acetamide sorbitol top agar and the overlay mixture was poured onto acetamide sorbitol plates for selection of transformants able to grow with acetamide as the sole nitrogen source. Plates were incubated at 28-30° C. until colonies appeared. Transformants were purified by repeat passage of single colonies on acetamide media (acetamide sorbitol recipe without the sorbitol).

Materials—
40 ml β-D-glucanase Solution: 600 mg β-D-glucanase; 400 mg MgSO$_4$.7H$_2$0 and 40 ml 1.2 M sorbitol.
200 ml PEG Mix: 50 g PEG 4000 (BDH Laboratory Supplies Poole, England) and 1.47 g CaCl$_2$ 2H$_2$0 made up in Milli Q water
Sorbitol/CaCl$_2$: 1.2M Sorbitol and 50 mM CaCl$_2$
For amdS selection, Acetamide Sorbitol plates and overlays were used. For spore purification, the same plates were used, but without sorbitol.
Acetamide Sorbitol Agar (Plates and Top Agar)
Acetamide (Aldrich 99% sublimed)—0.6 g/L; CsCl—1.68 g/L; Glucose—20 g/L; KH$_2$PO$_4$—20 g/L; MgSO$_4$.7H$_2$O—0.6 g/L; CaCl$_2$.2H$_2$O—0.6 g/L; 1000× salts (see below)—1 ml. pH adjusted to 5.5 and volume brought to 300 ml. Filter sterilized with 0.22 micron filter and warmed to 55° C. in an oven.
To 700 ml water Noble Agar (low-melt for top agar) 20 g and Sorbitol 218 g was added and then autoclaved. This mixture was cooled to 55° C., and filter sterilized, acetamide mix was added. Plates or tubes were poured.
1000× Salts—FeSO$_4$.7H$_2$O (0.5 g/100 ml); MnSO$_4$.H$_2$O (0.16 g/100 ml); ZnSO$_4$.7H$_2$O (0.14 g/100 ml); CoCl$_2$.6H$_2$O (0.1 g/100 ml) and filter sterilize with 0.22 micron filter.
Potato Dextrose Agar (PDA Difco Dehydrated Culture Media)—Potatoes, infusion from 200 g/L; Dextrose, 20 g/L and Agar, 15 g/L were mixed well in 50-80% final volume of dH$_2$O, and then brought to 100% final volume. This mixture was autoclaved, cooled to 55° C. and poured.

To make up 1% skim milk agar for a pH 3.5 media PDA was prepared as above and to 100 ml molten PDA, 1.8 ml 10% tartaric acid and 12.5 ml sterilized 8% skim milk was added and plates were poured. To pre-sterilize skim milk, 8% skim milk (Difco) was autoclaved for 10 minutes, 122-123° C., and chamber pressure during exposure of 32-35 psi. The mixture was removed, cooled and stored at room temperature.

Protease Expression was evaluated in transformants after 3 days growth in shake flasks. *T. reesei* culture media (Davis, et al., (1970) Methods Enzymol. 17:79-143) was inoculated with an agar plug. Cultures were incubated for 3 days at 30° C., with shaking. Culture broth was passed through a 0.22 micron filter, and the filtrate spotted onto 1% Skim milk agar. Clearing zones were observed following overnight incubation at room temperature.

during the entire fermentation period. Samples were removed during the fermentation for HPLC analysis using HPLC column: Phenomenex Rezex Organic Acid Column (RHM-Monosaccharide) #00H 0132-KO (Equivalent to Bio-Rad 87H); Column temperature: 60 C; Mobile Phase: 0.01N $H_2SO_4$; Flow rate 0/6 mL/min; Detector: RI; and Injection Volume: 20 uL. The fermentation was terminated after 72 hours. The HPLC profiles for sugars, lactic acids glycerol and ethanol at various sample intervals is shown in Table 1. The mash was dried at 60° C. to obtain the DDGS and the starch content of the DDGS was determined by the dual enzyme method.

TABLE 1

% Ethanol Production and % Residual Starch in Fermentation with or without NSP24

| GA-source | NSP24 | % EtOH 17 hr | % EtOH 25 hr | % EtOH 49 hr | % EtOH 65 hr | % EtOH 72 hr | % Residual Starch 72 hr |
|---|---|---|---|---|---|---|---|
| AnGA | | | | | | | |
| Whole ground corn | – – | 9.18 | 10.51 | 16.16 | 17.77 | 17.67 | 3.38 |
| | + | 10.52 | 11.87 | 17.61 | 18.41 | 18.60 | 2.03 |
| Endosperm | – – | 7.73 | 9.91 | 14.01 | 15.46 | 15.69 | 2.89 |
| | + | 11.06 | 13.61 | 17.31 | 18.24 | 18.34 | 0.55 |
| TrGA | | | | | | | |
| Whole ground corn | – – | 7.73 | 9.93 | 14.00 | 15.95 | 16.36 | 8.45 |
| | + | 8.11 | 10.51 | 15.04 | 17.05 | 17.40 | 6.49 |
| Endosperm | – – | 7.31 | 9.47 | 13.31 | 14.91 | 15.33 | 4.50 |
| | + | 10.51 | 12.97 | 17.11 | 17.95 | 18.14 | 1.15 |

The addition of NSP24 to the yeast fermentation medium containing granular starch substrate resulted in a higher level of alcohol and a lower level of residual starch content in the DDGS. The effect is even more pronounced with the fractionated corn endosperm compared to whole ground corn.

Example 2

Effect of Protease During Hydrolysis of Granular Starch Substrate

Ground corn (#2 Yellow Dent), which is typically used in the ethanol industry was fractionated to obtain the endosperm fraction. Both the corn and endosperm/gluten fraction were ground to obtain a sample that would pass >95% through a 1.5 mm screen (Perten Laboratory Mill 3100, Sweden). The moisture content and the total starch content of whole ground and endosperm fractions were determined (each flask contained equal amounts of starch (32% DS for ground corn and 29.9% DS for the endosperm fraction). The pH was adjusted to 4.2 using $6NH_2SO_4$. AnGA (DISTILLASE L-400, Genencor International, Inc.) or a TrGA added at 1.0 GAU/g ds and acid stable alpha amylase from *Aspergillus kawachi* (AkAA) obtained from expression in *Trichoderma* as described in USP 2005/0266543 was added at 3 SSU/g DS. NSP24 was added at 0.5 SAPU/g DS along with 400 ppm urea. 5.0 g Red Start Ethanol Red dry yeast (Lesaffre Yeast Corporation, Milwaukee, Wis.) in 45 ml of DI $H_2O$ was prepared and mixed in a 32 C water bath for 1 hour prior to inoculating the reaction flasks with 0.5 ml of the yeast slurry. The flasks were placed in a 32° C. water bath and the mash (slurry) mixed gently Example 3

Effect of Protease on the Alcohol Yield and the Residual Starch Content of the DDGS During the Fermentation of Granular Starch Containing Substrates, Whole Ground Corn and Fractionated Corn (Degermed Corn) with Different Particle Sizes Yellow Dent corn #2 was ground to obtain ground whole corn with varying particle sizes using a laboratory scale hammer mill (Perten Laboratory Mill 3100, Sweden) and degermed corn was used as an example for fractionated corn. The particle size distribution was measured using a standard sieve with different pore sizes. In Table 2 below 95% means about 95% of the particles passed through a 30 mesh screen (0.59 mm) and about 5% did not pass through the screen; they were retained on the screen; 70% means about 70% of the particles passed through a 30 mesh screen (0.59 mm) and about 30% did not pass through the screen; they were retained on the screen; and 50% means about 50% of the particles passed through a 30 mesh screen (0.59 mm) and about 50% did not pass through the screen; they were retained on the screen. Determinations were also made of the moisture content and the total starch content of whole ground corn. Fermentations were conducted in 125 ml flasks containing 100 g mash of ground whole corn (32% ds) or degermed fractionated corn (29.6% ds). Urea (400 ppm) was added to each of the reaction flasks and the pH was adjusted to 4.2 using 6 N $H_2SO_4$. STARGEN™ 001, was added at 2.5 kg/MT corn DS. NSP24 was added at 0.5 SAPU/g ds. Five grams of Red Star Ethanol Red dry yeast (Lesaffre Yeast Corporation, Milwaukee, Wis.) in 45 mls of water was prepared and mixed in a 32° C. water bath for one hour prior to inoculating the flask; 0.5 ml of this yeast slurry was added to each flask. The flasks were placed in a 32° C. water bath and the mash mixed gently during the entire fermentation period. Samples were removed during fermentation for HPLC analysis using HPLC Column: Phenomenex Rezex Organic Acid Column (RHM-Monosaccharide) #00H 0132-KO (Equivalent to Bio-Rad 87H); Column Temperature: 60° C.; Mobile Phase: 0.01 N $H_2SO_4$; Flow Rate: 0.6 mL/min; Detector: RI; and Injection Volume: 20 μL. The fermentations were terminated after 72 hours. The yeast fermentations produced a number of compounds including sugars, lactic acid, glycerol and ethanol at various sampling intervals and some of the levels as determined by HPLC are shown below. The mash was dried at 60° C. to obtain the DDGS, and the starch content of the DDGS at the 72 hour fermentation broth was determined by the dual enzyme method.

From the table it is observed that protease addition during the fermentation of the granular starch substrates (whole ground corn or fractionated corn) is a higher alcohol yield and lower residual starch in the DDGS. The effect is even more pronounced with coarser ground particles for ground whole or fractionated corn. These results suggest that the addition of protease allows one to use a coarser particle size of the grain substrates.

Example 4

Effect of Protease Concentration During Fermentation with a Medium Containing a Degermed Ground Corn Fraction (Endosperm)

100 g of a 29.5% DS mash of endosperm (degermed corn, 75.8% starch, particle size of 99.5%<30 mesh) was transferred to a 125 ml flask, 400 ppm of urea was added and the pH was adjusted to pH 4.5. NSP24 (1.0 SAPU/g ds) was added and followed by the addition of STARGEN 001 (Genencor International) at 2.8 Kgs/MT of starch. Flasks were inoculated with 0.5 ml of 20% yeast (Red Star Ethanol Red) and then placed in a water bath maintained at 32° C. The contents of the flasks were continuously stirred for uniform

TABLE 2

Effect of NSP24 on the ethanol yield and the residual starch content of the DDGS during the fermentation of granular starch containing whole ground corn or fractionated corn containing different particle sizes

|  | NSP24 | % EtOH 24 hr | % EtOH 48 hr | % EtOH 71 hr | % Residual Starch DDGS 72 hr |
|---|---|---|---|---|---|
| Whole ground Corn Particle size * |  |  |  |  |  |
| 95% | – – | 11.33 | 15.19 | 15.73 | 9.08 |
|  | + | 13.53 | 17.47 | 17.46 | 7.72 |
|  |  |  |  | (1.73) |  |
| 70% | – – | 11.23 | 15.47 | 16.82 | 4.66 |
|  | + | 14.24 | 17.81 | 18.03 | 2.37 |
|  |  |  |  | (1.21) |  |
| 50% | – – | 10.85 | 14.96 | 16.49 | 26.21 |
|  | + | 12.69 | 16.84 | 17.67 | 13.83 |
|  |  |  |  | (1.18) |  |
| Corn Endosperm Particle Size * |  |  |  |  |  |
| 95% | – – | 7.91 | 12.71 | 14.77 | 10.35 |
|  | + | 13.85 | 17.93 | 18.27 | 2.00 |
|  |  |  |  | (3.50) |  |
| 70% | – – | 7.51 | 12.42 | 14.60 | 17.78 |
|  | + | 13.47 | 17.68 | 18.38 | 1.18 |
|  |  |  |  | (3.78) |  |
| 50% | – – | 7.74 | 12.59 | 14.80 | 11.20 |
|  | + | 13.33 | 17.03 | 17.99 | 1.63 |
|  |  |  |  | (3.19) |  |

1. * is defined in example 3
2. + represents samples with NSP24 and – – represents samples without NSP24 addition.
3. ( ) represents the difference in the ethanol yield at 71 hrs between the +NSP24 samples and the – –NSP24 samples for the same granular starch substrate and the same particle size.

mixing during incubation. Samples were taken at different intervals of time for HPLC analysis. The residual starch and protein content of the DDGS at 72 hours was determined and some of the results are shown below.

TABLE 3

Effect of protease addition during the fermentation medium containing degermed fractionated corn on the final alcohol yield and residual starch in the DDGS.

| NSP24 kg/MT | Urea ppm | hrs | % w/v DP > 2 | % w/v DP – 1 | % v/v EtOH | % Starch DDGS |
|---|---|---|---|---|---|---|
| 0 | 400 | 22 | 0.24 | 2.72 | 10.15 | 11.62 |
|  |  | 46 | 0.21 | 2.92 | 14.57 |  |
|  |  | 72 | 0.18 | 1.35 | 16.45 |  |
| 0.09 | 400 | 22 | 0.24 | 1.67 | 11.70 | 1.67 |
|  |  | 46 | 0.18 | 1.13 | 16.11 |  |
|  |  | 72 | 0.16 | 0.01 | 17.60 |  |
| 0.13 | 400 | 22 | 0.24 | 1.41 | 12.44 | 0.57 |
|  |  | 46 | 0.19 | 1.14 | 16.33 |  |
|  |  | 72 | 0.21 | 0.01 | 17.49 |  |
| 0.26 | 400 | 22 | 0.21 | 0.92 | 13.17 | 0.49 |
|  |  | 46 | 0.18 | 0.04 | 17.39 |  |
|  |  | 72 | 0.19 | 0.01 | 17.96 |  |
| 0.43 | 400 | 22 | 0.21 | 0.77 | 13.10 | 0.35 |
|  |  | 46 | 0.18 | 0.02 | 17.48 |  |
|  |  | 72 | 0.20 | 0.01 | 18.30 |  |
| 0.26 | 600 | 22 | 0.21 | 0.83 | 13.33 | 0.31 |
|  |  | 46 | 0.28 | 0.02 | 17.77 |  |
|  |  | 72 | 0.17 | 0.02 | 18.20 |  |
| 0.26 | 800 | 22 | 0.19 | 0.32 | 13.56 | 0.58 |
|  |  | 46 | 0.17 | 0.04 | 18.21 |  |
|  |  | 72 | 0.17 | 0.02 | 18.42 |  |
| 0.26 | 1000 | 22 | 0.21 | 0.60 | 13.62 | 0.34 |
|  |  | 46 | 0.18 | 0.01 | 18.15 |  |
|  |  | 72 | 0.18 | 0.01 | 18.57 |  |

As observed from the results illustrated above, the addition of NSP24 resulted in a reduction in the levels of residual starch content at the end of the fermentation. Addition of NSP24 to the fermentation medium containing non-cooked degermed fractionated corn also resulted in a faster fermentation rate and higher alcohol yield.

Example 5

Figure 5:
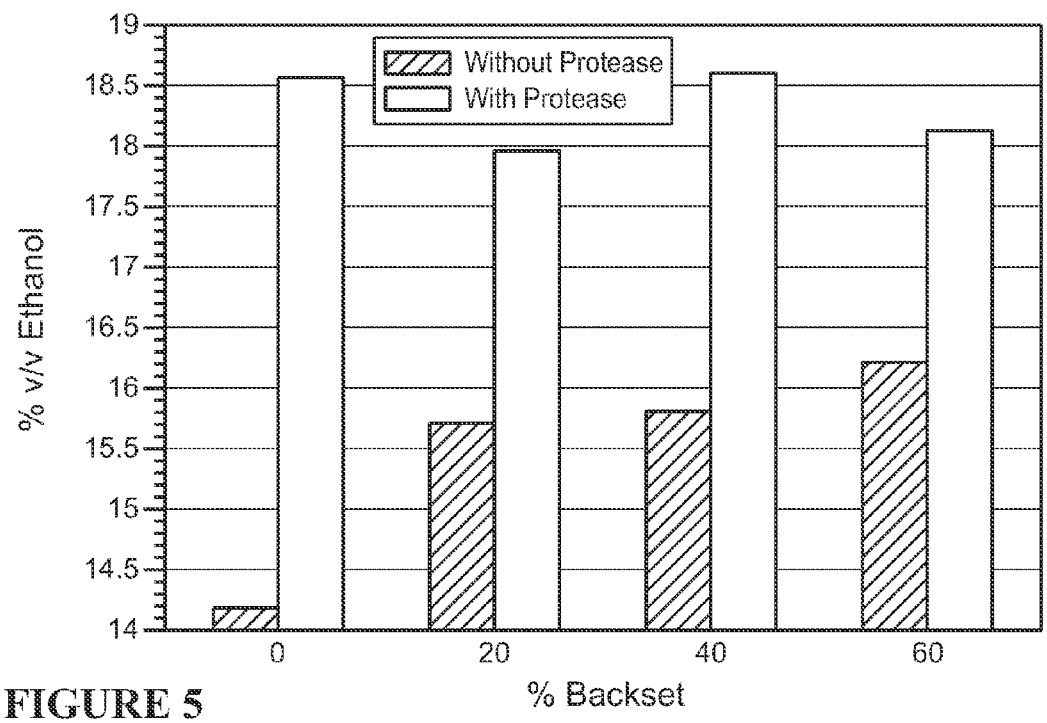
FIG. 5 illustrates the effect of NSP24 on % alcohol (v/v) production at 72 hrs during no cook yeast fermentations with fractionated corn endosperm and varying levels (%) of backset and reference is made to example 5.

Effect of Protease in a Yeast Fermentation Containing Granular Starch Substrate and Different Levels of Backset or Evaporator Concentrate A 30% ds mash in water and water containing different percentages of backset, wherein the backset was obtained from a typical dry grind conventional fermentation was were prepared using a fractionated corn endosperm (containing 78.51% starch DS and moisture content _%). Fermentations were conducted in 125 ml flasks containing 100 g mash of endosperm. The pH was adjusted to 4.2 using 6 N $H_2SO_4$. GA from DISTILLASE L-400 (Genencor International Inc) was added at 1.0 GAU/gds and an acid stable alpha amylase from *Aspergillus kawachi* (US Pat. Pub. 2005/0266543) was added at 3 SSU/g ds. NSP24 was added at 0.5 SAPU/g ds. Five grams of Red Star Ethanol Red dry yeast (Lesaffre Yeast Corporation, Milwaukee, Wis.) in 45 mls of water was prepared and mixed in a 32° C. water bath for one hour prior to inoculating the flask; 0.5 ml of the yeast slurry was added to each flask. The flasks were placed in a 32° C. water bath and the mash mixed gently during entire fermentation period. During the fermentation, samples were removed for HPLC analysis using HPLC Column: Phenomenex Rezex Organic Acid Column (RHM-Monosaccharide) #00H 0132-KO (Equivalent to Bio-Rad 87H); Column Temperature: 60° C.; Mobile Phase: 0.01 N $H_2SO_4$; Flow Rate: 0.6 mL/min; Detector: RI; and Injection Volume: 20 μL. The fermentations were terminated after 72 hours. The HPLC profile was determined for compounds produced during the fermentation including sugars, lactic acid, glycerol and ethanol at various sampling intervals. The mash was dried at 60° C. to obtain the DDGS, and the starch content of the DDG S from 72 hr fermentation broth was determined by the dual enzyme method. Some of the data is presented below in Table 4 and FIG. 5.

TABLE 4

Effect of protease in a yeast fermentation containing fractionated corn as the granular starch substrate with different levels of backset or condensate water.

| % Backset | NSP24 | % v/v EtOH 21.5 hr | % v/v EtOH 28 hr | % v/v EtOH 53 hr | % v/v EtOH 72 hr | % Residual Starch DDGS at 72 hr |
|---|---|---|---|---|---|---|
| 0 | – – | 6.16 | 7.99 | 12.69 | 14.17 | 3.92 |
|  | + | 11.47 | 14.45 | 18.25 | 18.55 | 0.62 |
| 20 | – – | 7.68 | 19.81 | 14.22 | 15.71 | 4.31 |
|  | + | 12.56 | 15.13 | 19.01 | 17.96 | 0.52 |
| 40 | – – | 8.65 | 10.7 | 14.89 | 15.8 | 4.06 |
|  | + | 12.42 | 14.68 | 18.72 | 18.6 | 0.88 |
| 60 | – – | 9.72 | 11.41 | 15.56 | 16.22 | 3.71 |
|  | + | 11.77 | 14.48 | 18.31 | 18.12 | 1.39 |

Example 6

Figure 6:
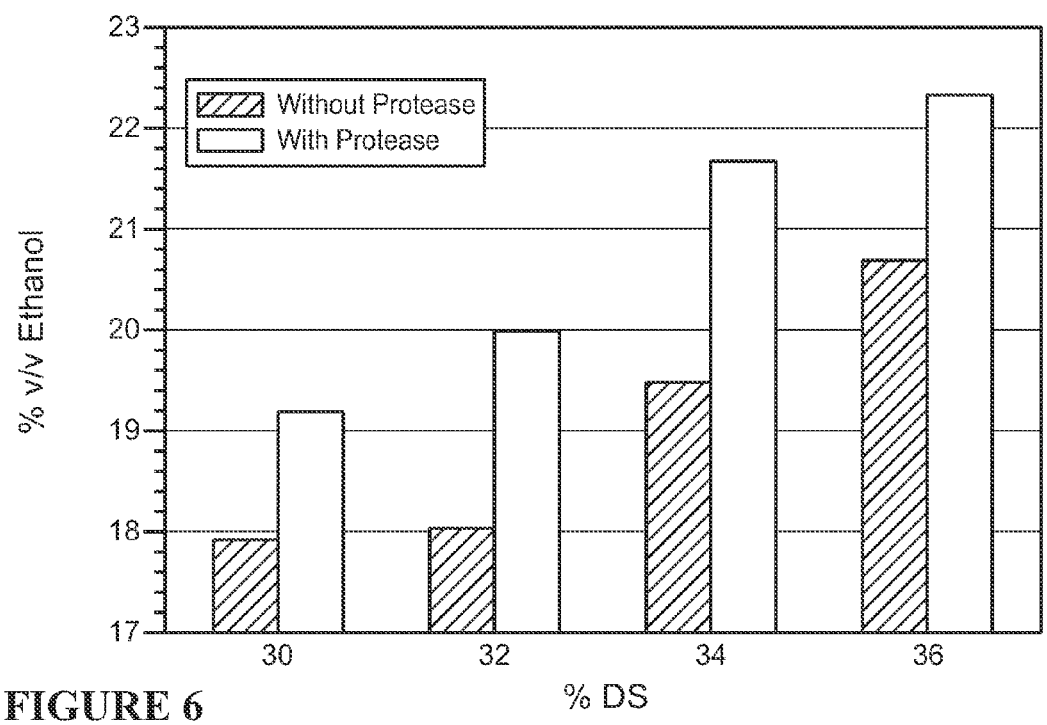
FIG. 6 illustrates the effect of NSP24 (0.7 SAPU/g ds) on % alcohol (v/v) production at 72 hrs during no cook yeast fermentations with different levels (% DS) of fractionated corn endosperm and reference is made to example 6.

Effect of Dry Solids (ds) of Fractionated Corn on the Final Alcohol Yield and the Residual Starch Under Yeast Fermentation Conditions with Added Protease The ground whole corn % DS was run at 32%, 34%, 36%, 38% and 40% and the fractionated corn endosperm % DS was run at 30%, 32%, 34% and 36%. Fermentations were conducted in 125 ml flasks containing 100 g mash of endosperm. The pH was adjusted to 4.2 using 6 N $H_2SO_4$. 400 ppm of urea was added and STARGEN™ 001 (Genencor International Inc.) was added at 1.39 GAU/g ds. NSP24 was added at 0.5 SAPU/g ds. Five grams of Red Star Ethanol Red dry yeast (Lesaffre Yeast Corporation, Milwaukee, Wis.) in 45 mls of water was prepared and mixed in a 32° C. water bath for one hour prior to inoculating the flask. 0.5 ml of the yeast slurry was added to each flask. The flasks were then placed in a 32° C. water bath for 36 hrs with continuous mixing and then the temperature of was decreased to 25° C. and maintained for 72 hours. During the fermentation, samples were removed for HPLC analysis under the conditions described in example 5. The fermentations were terminated after 72 hours. The HPLC profiles for the compounds produced during the fermentation, including sugars, lactic acid, glycerol and ethanol at various sampling intervals was determined. The mash was dried at 60° C. to obtain the DDGS, and the starch content of the DDG S from 72 hr fermentation broth was determined by the dual enzyme method. Some of the data is present in Table 5 and FIG. 6.

TABLE 5

Effect of NSP 24 and fractionated corn DS on the production ethanol and residual starch under yeast fermentation conditions with granular starch hydrolyzing enzymes

| %DS | NSP 24 | % Alcohol (v/v) | | | % Residual starch |
|---|---|---|---|---|---|
| | | 24 hr | 48 hr | 72 hr | 72 hr |
| 30 | - - | 9.99 | 14.76 | 17.91 | 18.41 |
| | + | 12.73 | 18.39 | 19.17 | 2.76 |
| 32 | - - | 10.23 | 15.55 | 18.01 | 12.47 |
| | + | 13.41 | 18.71 | 19.96 | 2.73 |
| 34 | - - | 10.79 | 16.2 | 19.46 | 15.05 |
| | + | 14.4 | 21.18 | 21.68 | 11.32 |
| 36 | - - | 12.32 | 17.78 | 20.69 | 15.73 |
| | + | 15.21 | 20.96 | 22.33 | 16.21 |

Example 7

Residual Starch and Ethanol Production with and without NSP24 Pretreatments at Different pH Levels A 29% ds whole ground corn substrate (de-oil) was prepared using tap water. The moisture content of the milled corn was 15.77%. For the pretreatment, the mash was adjusted to a pH of 4.5 or 3.7 at 60° C. in a water bath maintained for 60 min. Pretreatment (PT) included addition of STARGEN 001 (Genencor International, 0.75 GAU/g AnGA) with or without NSP24 dosed at 0.2 kg/MT. After pretreatment water was added to adjust for evaporation. The pretreated (PT) samples and samples of a milled corn slurry that was not pretreated (No PT) were transferred to a flask for yeast fermentation. The yeast fermentation was carried out by adding 400 ppm of urea and 0.75 GAU/g of STARGEN 001 in the presence of 0.2 kg/MT NSP24 or in the absence of NSP24 at either pH 4.5 or 3.7 at 30° C. Samples were taken at different time intervals for HPLC analysis of ethanol as previously described. The residual starch (RS) in the fermentation broth at 68 hours was measured using the dual enzyme method, and the results are shown below in Table 6.

TABLE 6

| Treatment | % v/v EtOH 24 hrs | % v/v EtOH 43 hrs | % v/v EtOH 50 hrs | % v/v EtOH 68 hrs | % RS |
|---|---|---|---|---|---|
| PT pH 4.5 (−NSP24) | 10.33 | 14.31 | 14.64 | 15.04 | 8.36 |
| PT pH 4.5 (+NSP24) | 10.48 | 13.64 | 14.34 | 14.84 | 9.12 |
| PT, pH 3.7 (−NSP24) | 10.52 | 13.61 | 14.32 | 14.90 | 8.80 |
| PT pH 3.7 (+NSP24) | 10.82 | 14.57 | 15.06 | 16.23 | 5.81 |
| No PT pH 4.5 (−NSP24) | 9.89 | 12.94 | 13.50 | 14.31 | 12.81 |
| No PT, pH 4.5 (+NSP24) | 9.85 | 13.19 | 14.37 | 14.65 | 11.90 |
| No PT, pH 3.7 (−NSP24) | 9.98 | 13.35 | 13.93 | 14.75 | 11.22 |
| No PT, pH 3.7 (+NSP 24) | 10.41 | 14.03 | 14.74 | 15.66 | 10.45 |

The invention claimed is:

1. A method for decreasing the amount of residual starch produced from fermentation of granular starch containing substrates comprising
fermenting a granular starch containing substrate with a NSP24 protease, a granular starch hydrolyzing enzyme and a fermenting microorganism, wherein the granular starch containing substrate is not cooked, wherein the NSP24 protease has at least 93% amino acid identity to SEQ ID NO: 3, and
obtaining a fermented broth wherein the % residual starch in the broth is decreased compared to the amount of residual starch obtained from a substantially similar method without the protease.

2. The method according to claim 1, wherein the granular starch containing substrate is a milled grain.

3. The method according to claim 2, wherein the milled grain is fractionated corn grain.

4. The method according to claim 1, wherein the fermented broth comprises less than 15% residual starch.

5. The method according to claim 1, further comprising recovering the distillers dried grain with solubles from the fermented broth.

6. A method of increasing ethanol production in a no cook fermentation comprising contacting a milled insoluble starch substrate with a granular starch hydrolyzing enzyme, an NSP24 protease, and a fermenting microorganism under suitable fermentation conditions at a temperature below the starch gelatinization temperature of the substrate to produce ethanol wherein the ethanol production is increased compared to a substantially similar method conducted without the NSP24 protease, and wherein the NSP24 protease has at least 93% amino acid identity to SEQ ID NO: 3.

7. The method according to claim 6, wherein the increase in ethanol produced is at least 0.5% v/v.

8. A method of producing ethanol in a no cook simultaneous saccharification and fermentation which includes milled grain substrates comprising adding an NSP24 protease to the simultaneous saccharification and fermentation, wherein the NSP24 protease has at least 93% amino acid identity to SEQ ID NO: 3.

9. The method according to claim 8, wherein the milled grain substrate is fractionated corn endosperm.

10. The method according to claim 8, wherein the milled grain substrates have a particle size such that at least 50% fit through a 30 mesh screen.

11. The method according to claim 8 further comprising pretreating the milled grain substrate at a temperature of about 55° C. to 65° C. for about 30 minutes to 4 hours.

* * * * *